US010092263B2

(12) United States Patent
 Choi et al.

(10) Patent No.: US 10,092,263 B2
(45) Date of Patent: Oct. 9, 2018

(54) APPARATUS AND METHOD FOR GENERATING REPROJECTION IMAGES FOR DIAGNOSTIC FEATURE EXTRACTION

(71) Applicants: SAMSUNG ELECTRONICS CO., LTD., Suwon-si (KR); Korea Advanced Institute Of Science and Technology, Daejeon (KR)

(72) Inventors: Choong Hwan Choi, Suwon-si (KR); Yong Man Ro, Daejeon (KR); Dae Hoe Kim, Daejeon (KR); Seong Tae Kim, Daejeon (KR); Eun Joon Kim, Daejeon (KR)

(73) Assignees: SAMSUNG ELECTRONICS CO., LTD., Suwon-si (KR); Korea Advanced Institute Of Science and Technology, Daejeon (KR)

( * ) Notice: Subject to any disclaimer, the term of this patent is extended or adjusted under 35 U.S.C. 154(b) by 50 days.

(21) Appl. No.: 14/702,902

(22) Filed: May 4, 2015

(65) Prior Publication Data
 US 2015/0317820 A1    Nov. 5, 2015

(30) Foreign Application Priority Data

May 2, 2014    (KR) .................... 10-2014-0053521

(51) Int. Cl.
 *G06K 9/00*    (2006.01)
 *A61B 6/00*    (2006.01)
 (Continued)

(52) U.S. Cl.
 CPC ............ *A61B 6/5217* (2013.01); *A61B 6/502* (2013.01); *G06K 9/4604* (2013.01);
 (Continued)

(58) Field of Classification Search
 None
 See application file for complete search history.

(56) References Cited

U.S. PATENT DOCUMENTS 5,734,384 A * 3/1998 Yanof ..................... G06T 17/10
 345/419
6,337,992 B1 * 1/2002 Gelman ................. A61B 6/481
 128/899
(Continued)

FOREIGN PATENT DOCUMENTS

JP      07-028976 A  *   1/1995
WO    2008/035286 A2     3/2008
 (Continued)

OTHER PUBLICATIONS

Kanazawa, K., Kawata, Y., Niki, N., Satoh, H., Ohmatsu, H., Kakinuma, R., . . . & Eguchi, K. (1998). Computer-aided diagnosis for pulmonary nodules based on helical CT images. Computerized medical imaging and graphics, 22(2), 157-167.*
 (Continued)

*Primary Examiner* — Vu Le
*Assistant Examiner* — Samah Beg
(74) *Attorney, Agent, or Firm* — Sughrue Mion, PLLC

(57) ABSTRACT

A medical imaging apparatus includes a scanner configured to acquire projection data of an object in a plurality of directions, and a data processor configured to generate a volume of interest based on the projection data, generate a two-dimensional (2D) reprojection image by reprojecting the volume of interest in at least one direction, and extract feature information from the 2D reprojection image.

19 Claims, 28 Drawing Sheets

(51) Int. Cl.

| | | |
|---|---|---|
| *G06T 15/08* | (2011.01) | |
| *G06K 9/46* | (2006.01) | |
| *G06T 11/00* | (2006.01) | |
| *A61B 6/02* | (2006.01) | |
| *A61B 6/03* | (2006.01) | |
| *A61B 6/04* | (2006.01) | |
| *G06K 9/50* | (2006.01) | |

(52) U.S. Cl.
CPC ............ *G06T 11/008* (2013.01); *G06T 15/08* (2013.01); *A61B 6/025* (2013.01); *A61B 6/032* (2013.01); *A61B 6/0414* (2013.01); *A61B 6/4035* (2013.01); *A61B 6/4233* (2013.01); *A61B 6/5205* (2013.01); *G06K 9/50* (2013.01); *G06T 2207/10116* (2013.01)

(56) References Cited

U.S. PATENT DOCUMENTS

| | | | |
|---|---|---|---|
| 7,035,450 B1* | 4/2006 | Muller | G06K 9/3233 |
| | | | 382/128 |
| 7,840,046 B2* | 11/2010 | Jerebko | A61B 6/466 |
| | | | 378/37 |
| 2002/0068863 A1 | 6/2002 | Slack | |
| 2004/0070584 A1* | 4/2004 | Pyo | G06T 7/60 |
| | | | 345/419 |
| 2005/0090733 A1 | 4/2005 | Van Der Lugt et al. | |
| 2005/0226486 A1* | 10/2005 | Tsujii | A61B 6/032 |
| | | | 382/132 |
| 2008/0150937 A1* | 6/2008 | Lundstrom | G06T 15/08 |
| | | | 345/419 |
| 2009/0034684 A1* | 2/2009 | Bernard | G06T 19/00 |
| | | | 378/98 |
| 2009/0123052 A1 | 5/2009 | Ruth et al. | |
| 2010/0166267 A1 | 7/2010 | Zhang et al. | |
| 2011/0052035 A1 | 3/2011 | Kirchberg et al. | |
| 2011/0142301 A1* | 6/2011 | Boroczky | G06T 7/0012 |
| | | | 382/128 |
| 2011/0150178 A1* | 6/2011 | Bernard | G06T 11/008 |
| | | | 378/22 |
| 2012/0121064 A1 | 5/2012 | Bernard | |
| 2013/0114371 A1* | 5/2013 | Inoue | A61B 8/08 |
| | | | 367/11 |
| 2014/0328531 A1* | 11/2014 | Lee | H04N 13/0275 |
| | | | 382/131 |
| 2014/0348387 A1* | 11/2014 | Choi | G06T 7/0012 |
| | | | 382/103 |
| 2015/0279034 A1* | 10/2015 | Knapp | G06T 11/008 |
| | | | 382/131 |

FOREIGN PATENT DOCUMENTS

| | | |
|---|---|---|
| WO | 2010059920 A2 | 5/2010 |
| WO | 2011/100511 A2 | 8/2011 |

OTHER PUBLICATIONS

Fishman, E. K., Ney, D. R., Heath, D. G., Corl, F. M., Horton, K. M., & Johnson, P. T. (2006). Volume Rendering versus Maximum Intensity Projection in CT Angiography: What Works Best, When, and Why 1.Radiographics, 26(3), 905-922.*

Search Report dated Aug. 21, 2015, issued by the International Searching Authority in counterpart International Application No. PCT/KR2015/004447 (PCT/ISA/210).

Communication dated Dec. 7, 2017, issued by the European Patent Office in counterpart European Patent Application No. 15786774.8.

* cited by examiner

2D REPROJECTION IMAGE

2D REPROJECTION IMAGE

APPARATUS AND METHOD FOR GENERATING REPROJECTION IMAGES FOR DIAGNOSTIC FEATURE EXTRACTION

CROSS-REFERENCE TO RELATED APPLICATION

This application claims priority from Korean Patent Application No. 10-2014-0053521, filed on May 2, 2014, in the Korean Intellectual Property Office, the disclosure of which is incorporated herein in its entirety by reference.

BACKGROUND

1. Field

Apparatuses and methods consistent with exemplary embodiments relate to a medical imaging apparatus configured to extract features of an object from a three-dimensional (3D) image of the object and a controlling method thereof.

2. Description of Related Art

Medical imaging apparatuses are apparatuses that noninvasively acquire images of interior regions of an object by emitting X-rays or applying a magnetic field to the object. Medical imaging apparatuses include computed tomography (CT) apparatuses, positron emission tomography (PET), tomosynthesis, and magnetic resonance imaging (MRI) apparatuses.

Particularly, the medical imaging apparatus may generate three-dimensional (3D) volume data as well as two-dimensional (2D) sectional images of an object. A user may obtain morphological features of the interior regions of the object by using the 3D volume data and thus the 3D volume data may be useful in diagnostic applications.

SUMMARY

One or more exemplary embodiments provide a medical imaging apparatus capable of improving the accuracy of classifying lesions by extracting desired feature information from projection images, which are acquired by projecting 3D volume data of an object in at least one direction.

Additional aspects will be set forth in part in the description which follows and, in part, will be obvious from the description, or may be learned by practice of the exemplary embodiments.

In accordance with an aspect of an exemplary embodiment, a medical imaging apparatus includes a scanner configured to acquire projection data of an object from a plurality of views, and a data processor configured to generate a volume of interest based on the projection data, configured to generate at least one of 2D reprojection image by reprojecting the volume of interest in at least one direction, and configured to extract feature information from the at least one 2D reprojection image.

The data processor may determine whether a predetermined target substance exists in the volume of interest based on the extracted feature information.

The data processor may generate an X-axis reprojection image by reprojecting the volume of interest in an X-axis direction, a Y-axis reprojection image by reprojecting the volume of interest in a Y-axis direction and a Z-axis reprojection image by reprojecting the volume of interest in a Z-axis direction.

The reprojection may include maximum value projection.

The data processor may generate a 3D volume based on the projection data and may extract the volume of interest from the 3D volume.

The data processor may generate a feature vector by fusing the extracted feature information, and may determine whether a predetermined target substance exists in the volume of interest by applying a classifier to the generated feature vector.

The data processor may perform CAD (Computer Aided Diagnosis) based on the extracted feature information.

The data processor may generate a plurality of sectional images based on the projection data, and may further include a display configured to display at least one sectional image among the plurality of sectional images.

The medical imaging apparatus may further include an input unit configured to receive a setting of a region of interest of the displayed sectional image.

The data processor may extract a volume of interest corresponding to the set region of interest.

The display may display a region of interest, which corresponds to the volume of interest, on the displayed sectional image.

The display may display the at least one 2D reprojection image.

The display may display at least one of information related to a size of the region of interest, information related to a sectional image corresponding to the volume of interest, and a probability of the presence of a predetermined target substance in the volume of interest.

In accordance with an aspect of an exemplary embodiment, a medical imaging apparatus includes a data processor configured to generate a volume of interest based on projection data and configured to generate at least one 2D reprojection image by reprojecting the volume of interest in at least one direction, and a display configured to display the generated 2D reprojection image.

The data processor may generate a plurality of sectional images based on the projection data, and the display may display at least one sectional image among the plurality of sectional images.

The display may display a region of interest, which corresponds to the volume of interest, on the displayed sectional image.

The display may display the generated 2D reprojection image when the displayed region of interest is selected by a user.

The display may display at least one of information related to a size of the region of interest, information related to a sectional image corresponding to the volume of interest, and a probability of the presence of a predetermined target substance in the volume of interest when the displayed region of interest is selected by a user.

The data processor may determine whether a predetermined target substance exists in the volume of interest based on the extracted feature information.

The data processor may generate an X-axis reprojection image by reprojecting the volume of interest in an X-axis direction, a Y-axis reprojection image by reprojecting the volume of interest in a Y-axis direction and a Z-axis reprojection image by reprojecting the volume of interest in a Z-axis direction.

The display may display the X-axis reprojection image, the Y-axis reprojection image, and the Z-axis reprojection image.

The reprojection may include maximum value projection.

In accordance with an aspect of an exemplary embodiment, a control method of a medical imaging apparatus includes generating a volume of interest based on projection data of an object, generating at least one 2D reprojection image by reprojecting the volume of interest in at least one direction, extracting feature information from the at least one 2D reprojection image, and determining whether a predetermined target substance exists in the volume of interest based on the extracted feature information.

The generating at least one 2D reprojection image may include generating an X-axis reprojection image by reprojecting the volume of interest in an X-axis direction, generating a Y-axis reprojection image by reprojecting the volume of interest in a Y-axis direction and generating a Z-axis reprojection mage by reprojecting the volume of interest in a Z-axis direction.

The reprojection may include maximum value projection.

The determining whether a predetermined target substance exists in the volume of interest may include generating a feature vector by fusing the extracted feature information, and determining whether a predetermined target substance exists in the volume of interest by applying a classifier to the generated feature vector.

The generating a volume of interest based on projection data of an object may include generating a plurality of sectional images based on the projection data, generating a 3D volume based on the plurality of sectional images, and extracting the volume of interest from the 3D volume.

The control method may further include displaying at least one sectional image among the plurality of sectional images.

The control method may further include displaying a region of interest, which corresponds to the volume of interest, on the displayed sectional image.

The control method may further include displaying the generated 2D reprojection image when the displayed region of interest is selected by a user.

The control method may further include displaying at least one of information related to a size of the region of interest, information related to a sectional image corresponding to the volume of interest, and a probability of the presence of a predetermined target substance in the volume of interest when the displayed region of interest is selected by a user.

The control method may further include determining whether a predetermined target substance exists in the volume of interest based on the extracted feature information and displaying a result of the determination.

BRIEF DESCRIPTION OF THE DRAWINGS

The above and/or other aspects will become more apparent by describing certain exemplary embodiments with reference to the accompanying drawings, in which.

DETAILED DESCRIPTION

Figure 1:
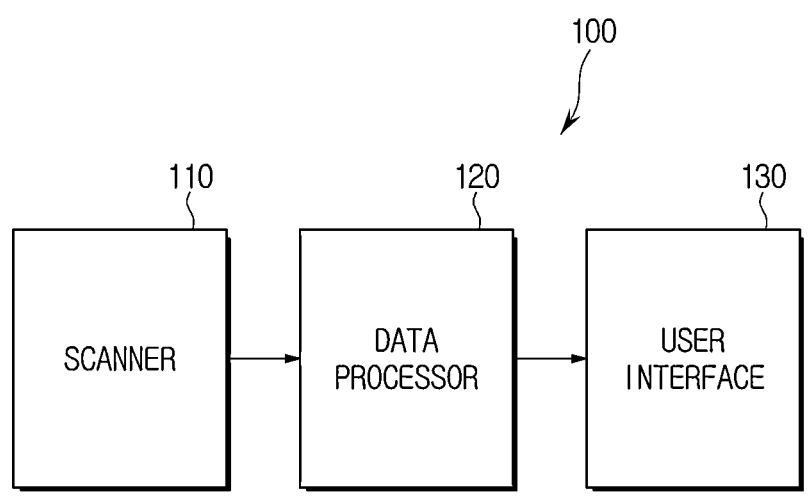
FIG. 1 is a control block diagram illustrating a medical imaging apparatus according to an exemplary embodiment.

Certain exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

FIG. 1 is a control block diagram illustrating a medical imaging apparatus according to an exemplary embodiment.

Referring to FIG. 1, a medical imaging apparatus 100 according to an exemplary embodiment may include a scanner 110 acquiring image data of an interior region of an object by scanning the object, a data processor 120 reconstructing a three-dimensional (3D) volume of the object based on the image data of the interior region of the object and extracting desired feature information from the 3D volume of the object, and a user interface 130 providing a result of the extracting the feature information to a user.

In an exemplary embodiment, an object may represent a part being examined for diagnosis by using the medical imaging apparatus 100. For example, when a chest is being examined for diagnosis, an object is a chest, and when a breast is being examined for diagnosis, an object is a breast. The object of the medical imaging apparatus 100 may include a living body including a human body, and an object may be imaged by the medical imaging apparatus 100.

The data processor 120 may reconstruct a 3D volume of an object based on image data acquired by the scanner 110, and may generate at least one reprojection image by reprojecting the 3D volume of the object in at least one direction among an X-axis, a Y-axis, and a Z-axis directions. Accordingly, the data processor 120 may extract predetermined feature information from at least one reprojection image.

As mentioned above, the scanner 110 may acquire an image of the interior region of the object by scanning the object. For this purpose, the scanner 110 may use X-rays, or magnetic resonance.

Particularly, the scanner 110 may perform any one of tomosynthesis, computed tomography (CT), and positron emission tomography (PET) by using X-rays or perform magnetic resonance imaging (MRI). In addition, the scanner 110 may perform a combination of more than two imaging techniques among the above mentioned techniques. Hereinafter, a configuration and operations of the scanner 110 performing different imaging techniques will be described.

FIGS. 2, 3, 4, and 5 are views illustrating a medical imaging apparatus in a case where a scanner performs tomosynthesis.

Tomosynthesis is a 3D breast imaging technique, more particularly, a technique to acquire a plurality of sectional images by emitting X-rays to a breast in various angles compared to conventional mammography acquiring a two-dimensional (2D) projection image by emitting X-rays to a breast in a limited angle.

Figure 2:
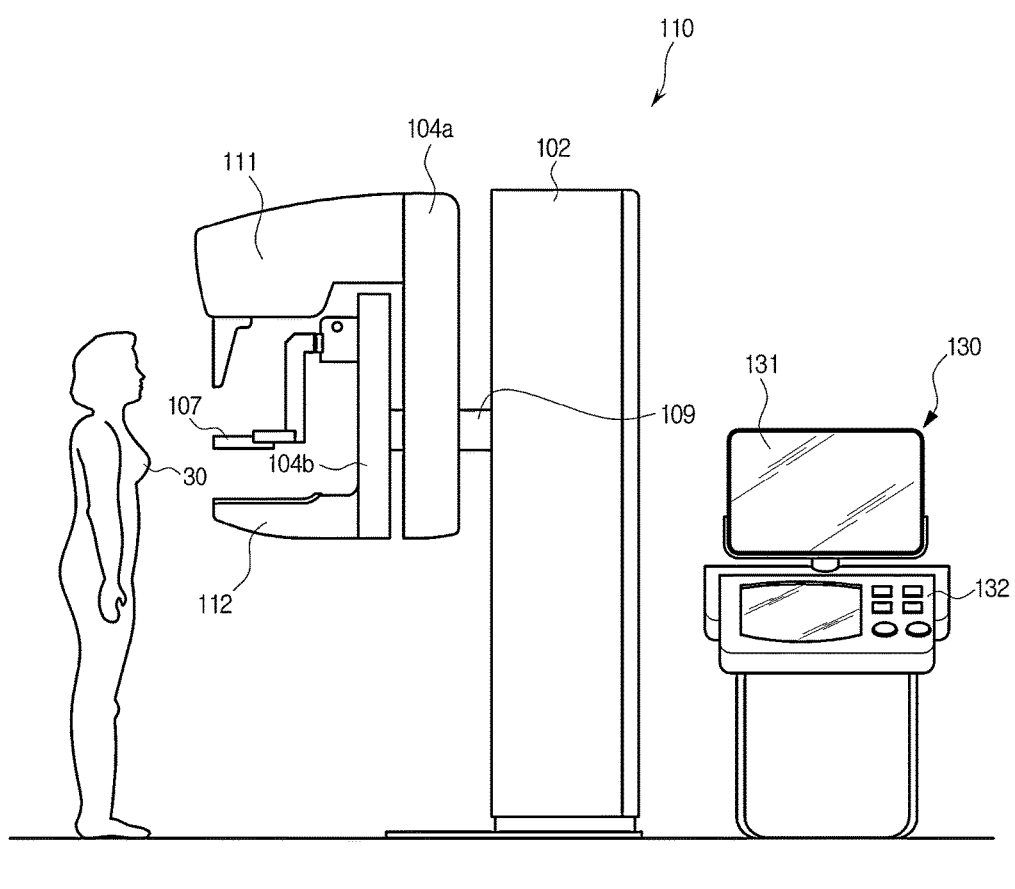
FIGS. 2, 3, 4, and 5 are views illustrating a medical imaging apparatus in which a scanner performs tomosynthesis.

Therefore, the scanner 110 may emit X-rays with respect to a breast that is an object 30 to perform tomosynthesis in various angles. For this purpose, the scanner 110 may have a structure, as illustrated in FIG. 2.

The scanner 110 may include an X-ray source 111 generating and emitting X-rays to the object 30 and an X-ray detector 112 detecting X-rays having penetrated the object 30. The X-ray source 111 may generate X-rays, and a configuration of the X-ray source 111 will be described later.

The breast 30 may be compressed to acquire clear images of the object 30 by using a compression paddle 107 since the breast 30 includes soft tissues. The compression paddle 107 may be moved upward and/or downward along a second arm 104b connected to the X-ray detector 112. When the breast 30 is placed on the X-ray detector 112, the compression paddle 107 may be moved downward to compress the breast 30 to have a certain thickness.

When the breast 30 is compressed, X-rays may be emitted from the X-ray source 111 and X-rays having penetrated the breast 30 may be detected by the X-ray detector 112. The X-ray detector 112 may acquire image data that is projection data from detected X-rays and may transmit the image data to the data processor 120 (see FIG. 1). The projection data may represent 2D projection data.

Figure 3:
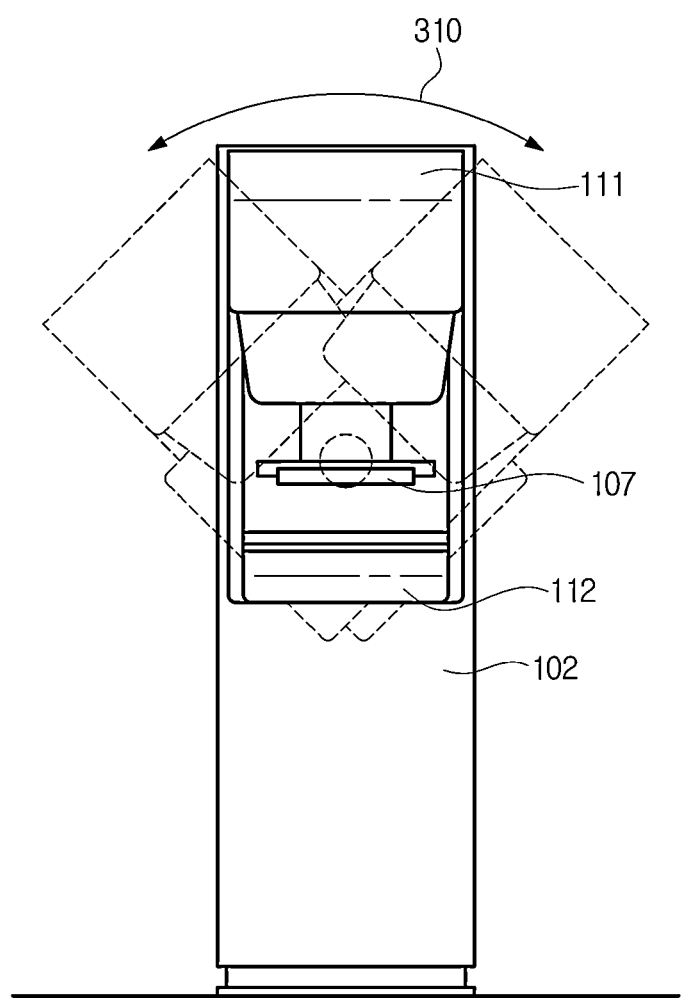

The scanner 110 may scan the object 30 in a plurality of views, which are different to each other. For this purpose, the X-ray source 111 may emit X-rays to the object 30 while a first arm 104a supporting the X-ray source 111 rotates within a certain angle with respect to a shaft 109 connected to a housing 102. At this time, the X-ray detector 112 may be fixed or rotated together with the X-ray source 111. However, when the scanner 110 has a structure as illustrated in FIG. 2, the X-ray detector 112 may be fixed and only the X-ray source 111 may be rotated in a direction 310 to the right or to the left within the certain angle, as illustrated in FIG. 3.

Figure 4:
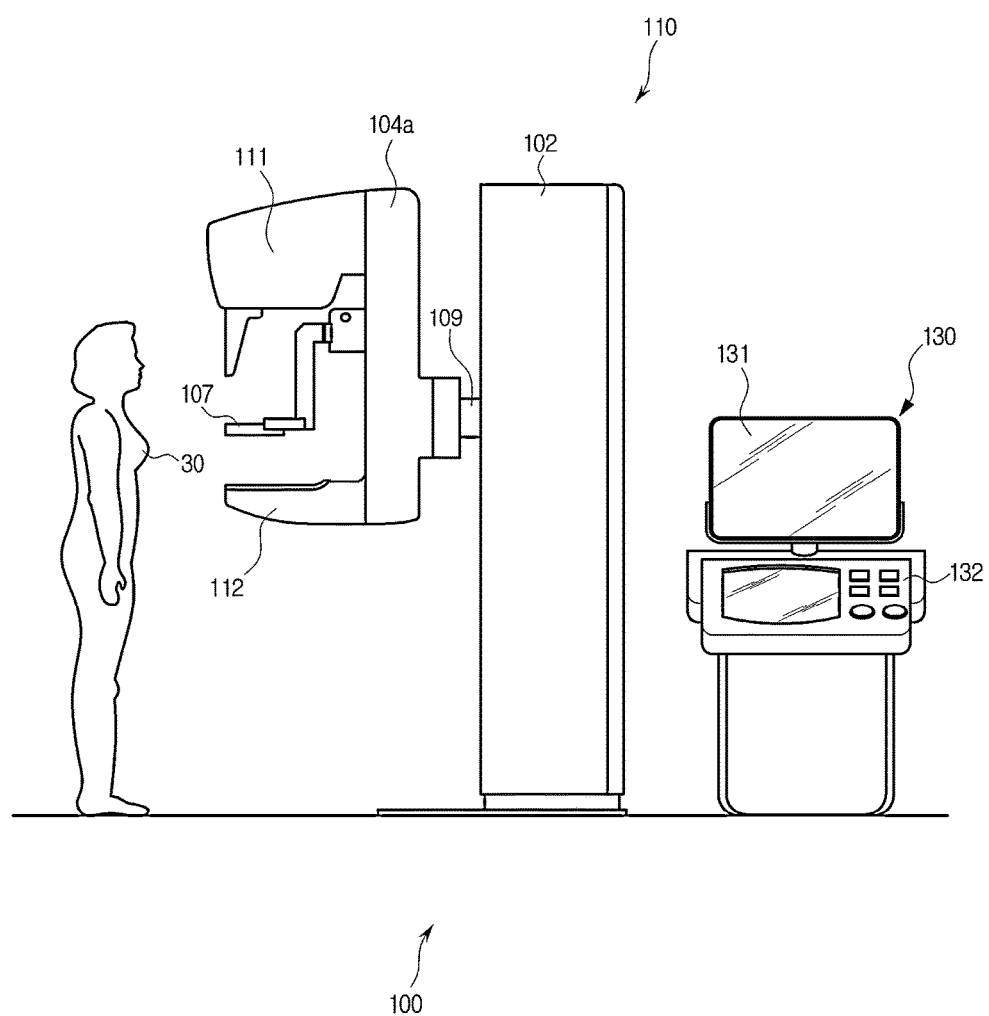
Figure 5:
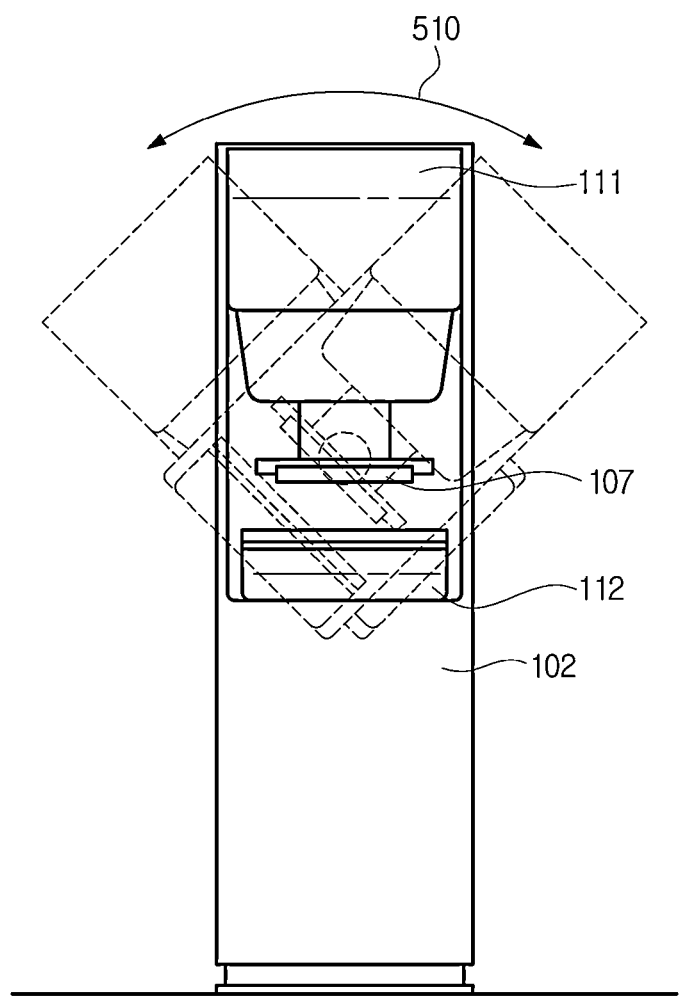

Alternatively, when the X-ray source 111 and the X-ray detector 112 are connected to the first arm 104a to be integrally formed as illustrated in FIG. 4, the X-ray source 111 and the X-ray detector 112 may be rotated together in a direction 510 to the right or to the left within the certain angle, as illustrated in FIG. 5.

The X-ray detector 112 may include an X-ray detector element detecting X-rays having penetrated the object 30 and an X-ray grid preventing X-rays from being scattered.

Figure 6:
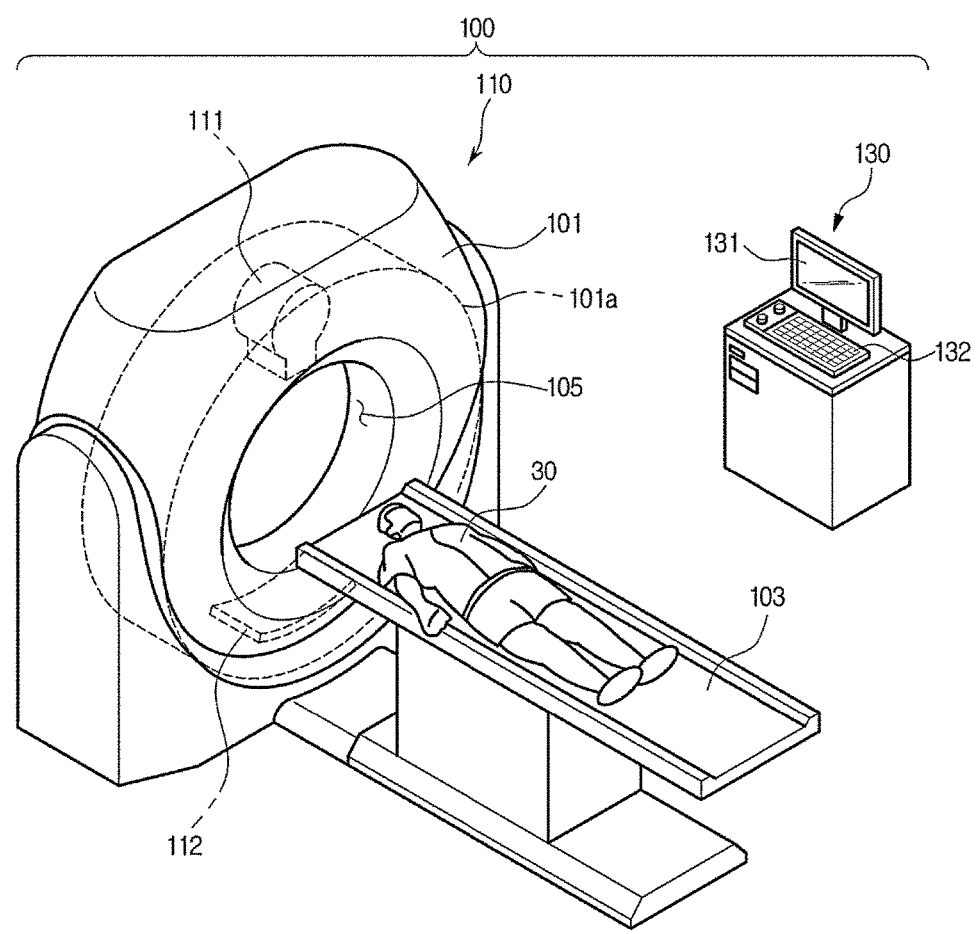
FIG. 6 is a view illustrating a medical imaging apparatus in which a scanner performs computed tomography.

FIG. 6 is a view illustrating a medical imaging apparatus in a case where a scanner performs computed tomography.

A scanner 110, which performs computed tomography, may include an x-ray source 111 emitting X-rays to an object 30, and an X-ray detector 112 detecting X-rays having penetrated the object 30. The X-ray source 111 and the X-ray detector 112 may be mounted to a gantry 101a while facing to each other, and the gantry 101a may be mounted within a housing 101.

When a table 103 where the object 30 is placed is moved into the inside of a bore 105 formed by the housing 101, the gantry 101a to which the X-ray source 111 and the X-ray detector 112 are mounted may scan the object 30 while rotating around the bore 105 in 360 degree rotation, and may acquire image data that is projection data. The projection data may represent a 2D projection image.

The medical imaging apparatus 100 according to exemplary embodiments of FIGS. 2 to 6 may include a user interface 130. The interface 130 may include a display 131 that is an output interface, and an input unit 132 that is an input interface.

The display 131 may include at least one of various display devices, such as a liquid crystal display (LCD), a light emission display (LED), an organic light emission display (OLED), a plasma display panel (PDP), and a cathode ray tube (CRT). The input unit 132 may include at least one of a keyboard, a mouse, a trackball, a key pad, a touch pad and the like.

A touch panel that is the input interface 132 may be disposed on the front of the display 131 that is the output interface 131 to be embodied as a touch screen.

The user interface 130 may be provided in a work station or a host device of the medical imaging apparatus 100.

Figure 7:
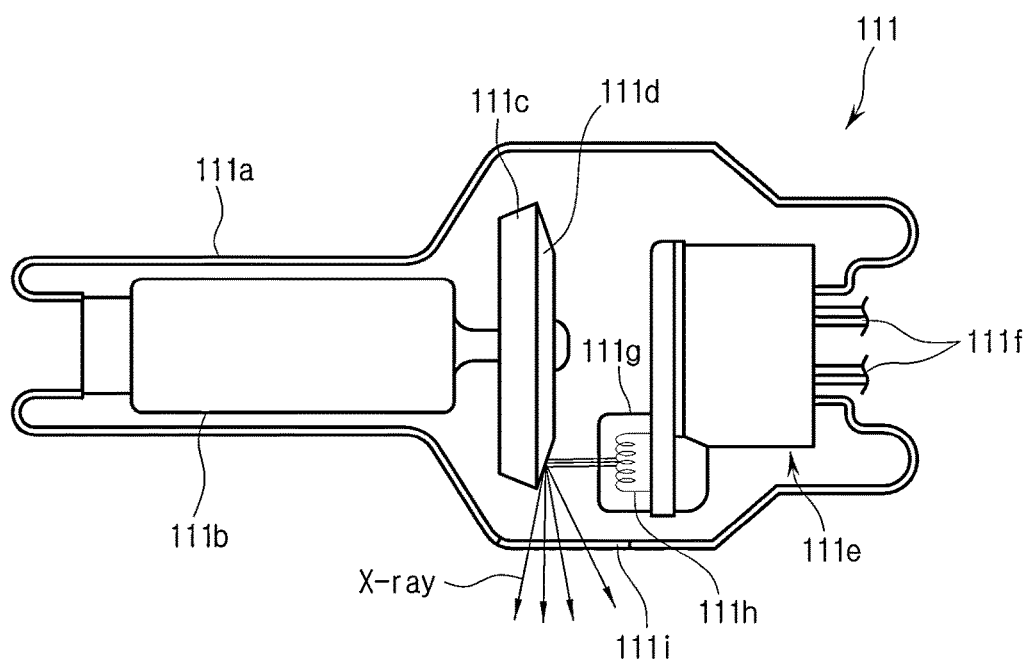
FIG. 7 is a view illustrating a configuration of an X-ray source.
Figure 8:
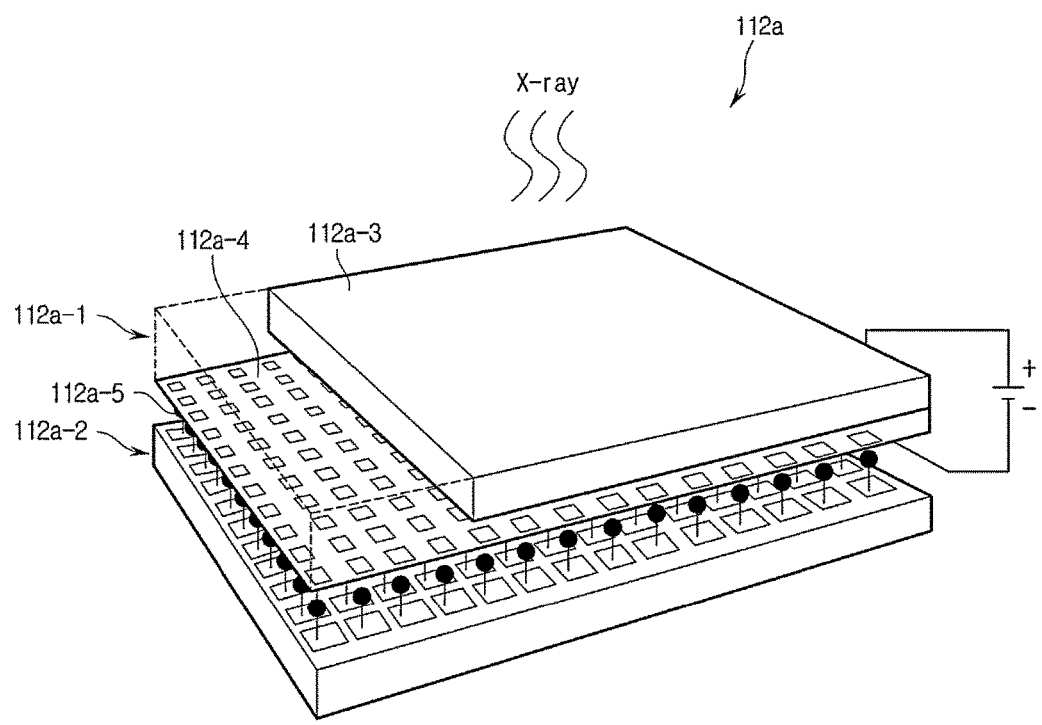
FIG. 8 is a view illustrating a configuration of an X-ray detector.

FIG. 7 is a view illustrating a configuration of an X-ray source, and FIG. 8 is a view illustrating a configuration of an X-ray detector.

When the X-ray source 111 emits X-rays, the X-ray source 111 may be embodied in a two-pole vacuum tube including an anode 111c and a cathode 111e. The cathode 111e may include filaments 111h and a focusing electrode 111g. The focusing electrode 111g may be referred to as a focusing cup.

A glass tube 111a may have a high vacuum state of approximately 10 mmHG that is formed inside the glass tube 111a and the filament 111h of the cathode 111e may be heated by a high temperature so that electrons may be generated. A tungsten filament may be used as the filament 111h, and the filament 111h may be heated by applying a current to an electrical conductor 111f connected to the filament 111h.

The anode 111c may include mainly copper, and a target material 111d may be applied to or placed on a side of the anode 111c, the side of the anode 111c facing the cathode 111e. The target material 111d may include high resistance materials, such as Cr, Fe, Co, Ni, W, and Mo. The melting point of the target material 111d may be higher, as a size of a focal spot is reduced. The focal spot may represent an effective focal spot. In addition, the target material 111d may be declined at a certain angle. Thus, the declination angle of the target material 111d may be smaller as the focal spot size decreases.

When a high voltage is applied between the cathode 111e and the anode 111c, an electron may be accelerated and collide with the target material 111d of the anode 111c, thereby generating X-rays. The generated X-rays may be emitted to the outside through a window 111i, and the window 111i may include a beryllium (Be) film. At this time, a filter may be disposed on a front surface or a rear surface of the window 111i to filter X-rays in a certain energy band.

The target material 111d may be rotated by a rotor 111b. When the target material 111d is rotated, the heat accumulation rate of the X-ray source 111 may be increased more than ten times per unit area as compared to when the target material 111d is fixed.

A voltage applied between the cathode 111e and the anode 111c of the x-ray source 111 may be referred to as a tube voltage, and a size of the tube voltage may be represented by a peak value (kvp). When the tube voltage is increased, a speed of the electrons may be increased, and thus an X-ray energy (or a photon energy), which is generated by collision between the electrons and the target material 111d, may be increased.

A current flowing through the X-ray source 111 may be referred to as a tube current, and the tub current may be represented by an average value in mA. When the tube current is increased, the number of electrons emitted from the filament 111h may be increased and thus the dose of X-rays (the number of X-ray photons), which are generated by collision between the electrons and the target material 111d, may be increased.

Therefore, the X-ray energy may be controlled by the tub voltage and the strength or the dose of X-rays may be controlled by the X-ray current and an X-ray exposure time. Accordingly, the energy and the strength of emitted X-rays may be controlled according to a type and features of the object 30.

When the emitted X-rays have a predetermined energy band, the energy band of the emitted X-rays may be defined by upper and lower limits. The upper limit of the energy band, i.e. the maximum energy of the emitted X-rays may be adjusted by the magnitude of the tube voltage, and the lower limit of the energy band, i.e., the minimum energy of the emitted X-ray may be adjusted by the filter. When the X-rays of low energy band are filtered by using the filter, the average energy of the emitted X-rays may be increased.

The X-ray detector 112 may acquire projection data of the object 30 by detecting the X-rays having penetrated the object 30, and may transmit the acquired projection data to the data processor 120. At this time, the projection data corresponding to a plurality of projection images of the object 30 may be transmitted to the data processor 120 since the object 30 may be scanned from a plurality of views at various angles with respect to the object 30.

The X-ray detector 112 which performs computed tomography may include a data acquisition system (DAS). The X-ray detector 112 may include a plurality of detectors mounted to a frame of the X-ray detector 112 in a shape of one dimensional array. A structure of the X-ray detector 112 will be described later in detail.

When the scanner 110 performs positron emission tomography, drugs in combination with radioisotopes emitting positrons are injected into a living body and the drugs are tracked by using the scanner 110 so that the distribution of the drugs in the body may be examined. In this case, an external appearance of the scanner 110 may be similar to that in a case of performing computed tomography, as illustrated in FIG. 6.

The emitted positron may be extinguished by combining with the electron in the periphery in the body, and gamma rays may be emitted in opposite directions while the positron is extinguished. The emitted gamma rays may penetrate living tissues, and the scanner 110 may include a radiation detector detecting the gamma rays having penetrated the living tissues. Since it may be difficult to predict which direction the gamma rays are to be emitted, the radiation detector in positron emission tomography may be arranged in a ring shape in which a plurality of radiation detectors surround the object.

Referring to FIG. 8, an X-ray detector 112a may include a light-receiving element 112a-1 converting the detected X-rays into an electrical signal and a readout circuit 112a-2 reading the electrical signal. The readout circuit 112a-2 may be formed in a two-dimensional pixel array including a plurality of pixel regions. The light-receiving element 112a-1 may include a single crystal semiconductor material, such as Ge, CdTe, CdZnTe, GaA, in order to ensure high resolution, fast response time and high dynamic range in a low energy and a low dose of X-rays.

The light-receiving element 112a-1 may be formed in a PIN photodiode in which a p-type layer 112a-4, in which a p-type semiconductor is arranged in a two-dimensional pixel, is boned to a lower portion of an n-type semiconductor substrate 112a-3 of high resistance. The readout circuit 112a-2 formed by using CMOS processes may be coupled to the light-receiving element 112a-1 for each pixel.

The CMOS readout circuit 112a-2 and the light-receiving element 112a-1 may be coupled to each other in a flip chip bonding method. For example, the CMOS readout circuit 112a-2 and the light-receiving element 112a-1 may be coupled to each other by forming bumps 112a-5, such as solder (PbSn) or indium (In), and reflowing and pressuring by applying heat to the bumps 112a-5.

However, the above-described structure of the X-ray detector 112a is only given as an example, and exemplary embodiments are not limited thereto. In addition to those described above, the X-ray detector 112a may have various structures according to a method of converting X-rays into electrical signals, and a method of collecting electrical signals.

Figure 9:
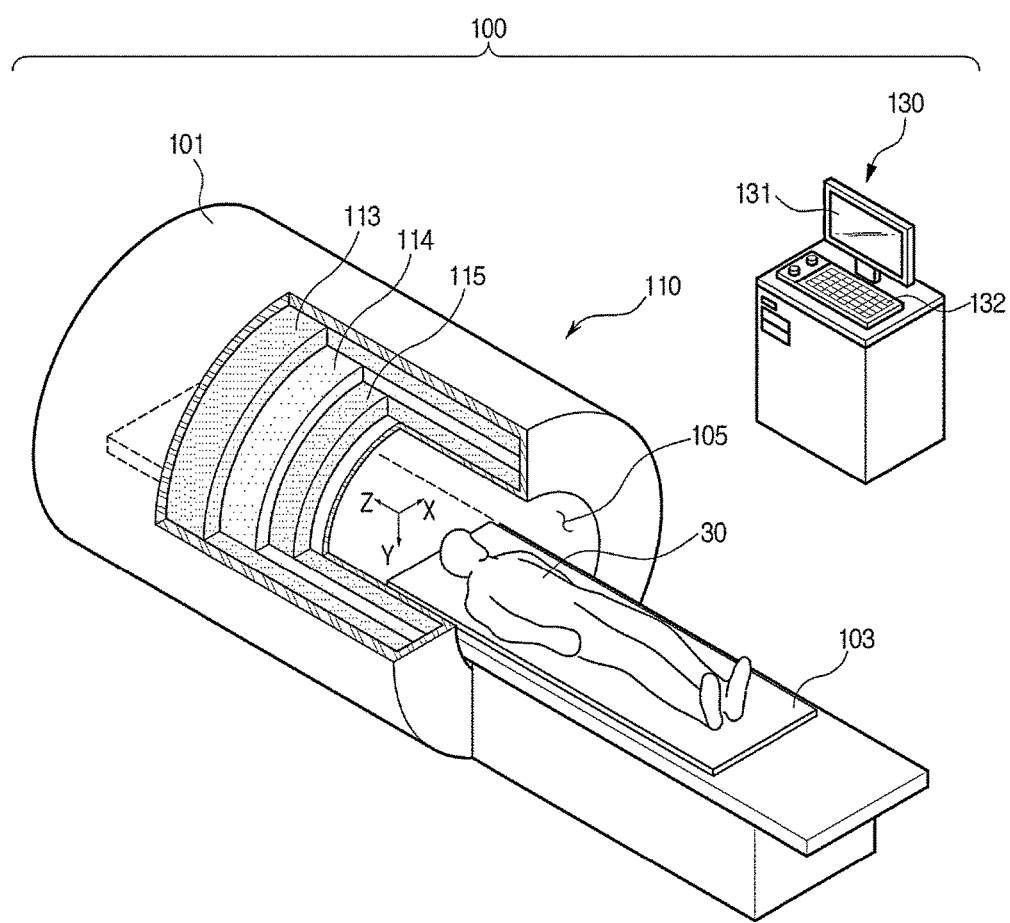
FIG. 9 is a view illustrating a medical imaging apparatus in which a scanner performs magnetic resonance imaging.

FIG. 9 is a view illustrating a medical imaging apparatus in a case where a scanner performs magnetic resonance imaging.

When using magnetic resonance, a scanner 110 may include a static magnetic field coil 113 mounted to an inner side of a housing 101, a gradient coil 114, and a radio frequency (RF) coil 115, as illustrated in FIG. 9.

The static magnetic field coil 113 may generate a static magnetic field in a bore 105, and the gradient coil 114 may form a gradient magnetic field by generating gradient to the static magnetic field. The RF coil 115 may apply an RF pulse to excite nuclei of an object 30 and receive echo signals from the nuclei.

That is, when a table 103, on which the object 30 is placed, is moved into the bore 105, the static magnetic field, the gradient magnetic field and the RF pulses may be applied to the object 30 so that nuclei constituting the object 30 may be excited and echo signals may be generated. The RF coil 115 may receive the echo signals and transfer the echo signals to the data processor 120 (see FIG. 1). The echo signal may represent image data.

As above, a configuration and operations of the scanner 110 configured to acquire image data by scanning an object is described in detail. Hereinafter, a configuration and operations of the data processor 120 configured to extract information related to the interior region of an object by processing data will be described in detail.

Figure 10:
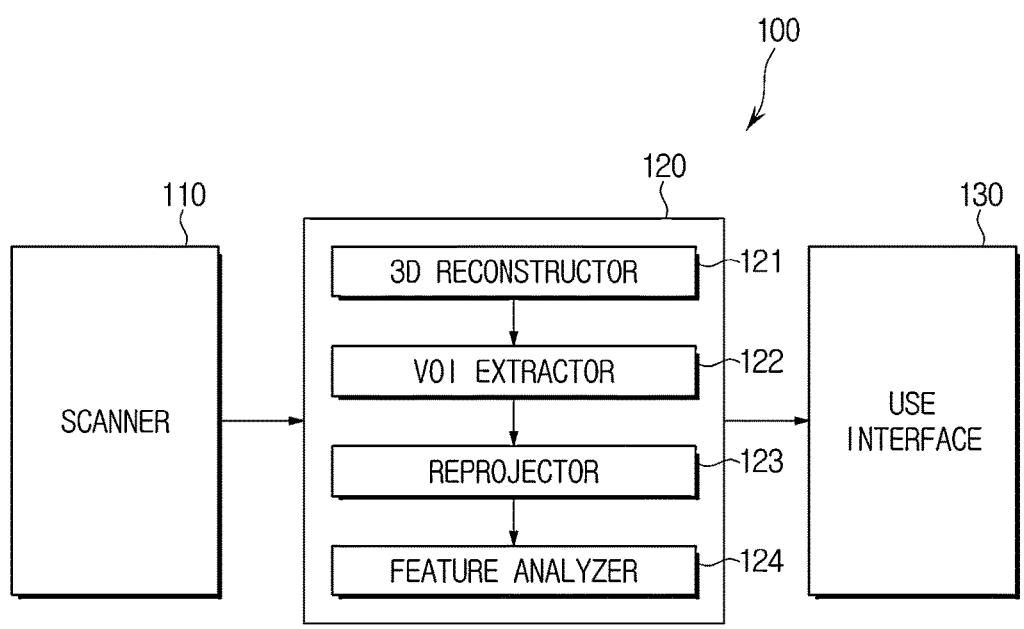
FIG. 10 is a control block diagram illustrating a configuration of a data processor according to an exemplary embodiment.

FIG. 10 is a control block diagram illustrating a configuration of a data processor according to an exemplary embodiment.

Referring to FIG. 10, the data processor 120 may include a 3D reconstructor 121 reconstructing a 3D volume based on projection data of an object, a volume of interest (VOI) extractor 122 extracting a VOI volume from the reconstructed 3D volume, a reprojector 123 generating at least one 2D reprojection image by reprojecting the extracted VOI volume in at least one direction, and a feature analyzer 124 extracting features from 2D reprojection images.

The data processor 120 may be embodied as a single processor or as an independent processor for each component. In addition, a plurality of components of the medical imaging apparatus 100 may be embodied in the same processor.

Figure 11:
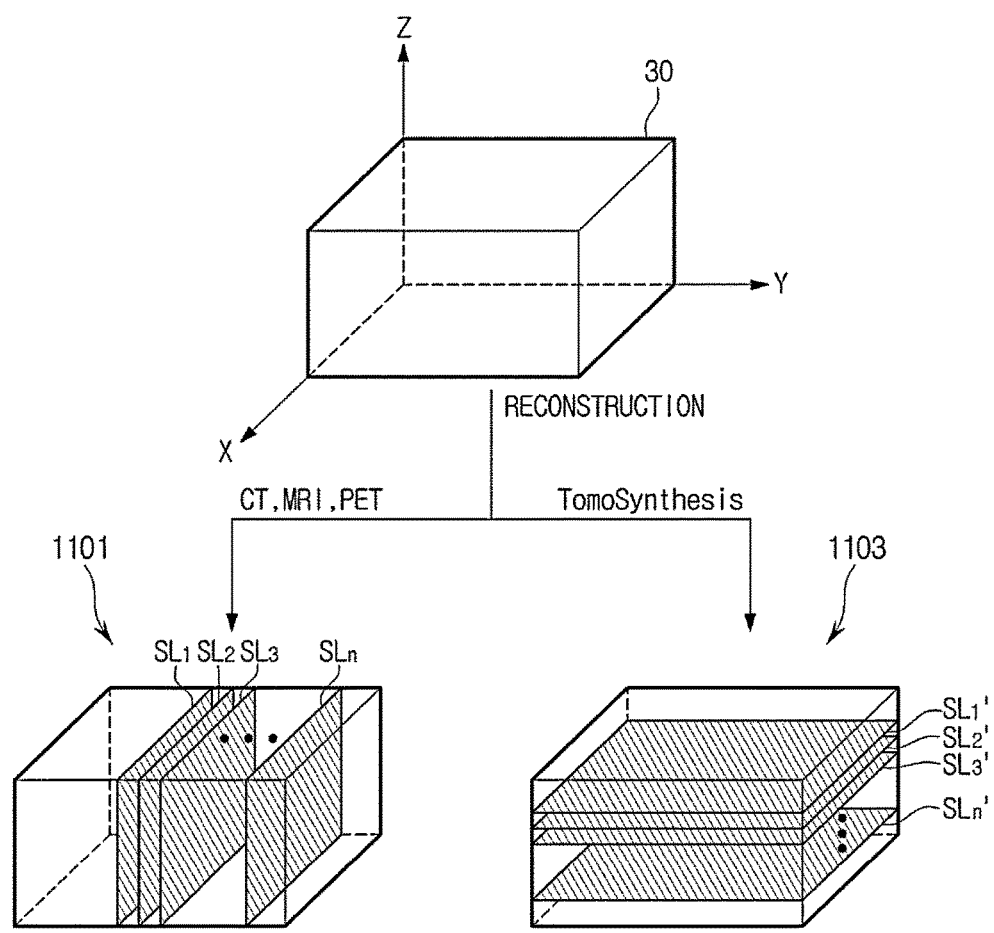
FIG. 11 is a view illustrating a sectional image of an object generated by a 3D reconstructor according to an exemplary embodiment.
Figure 12:
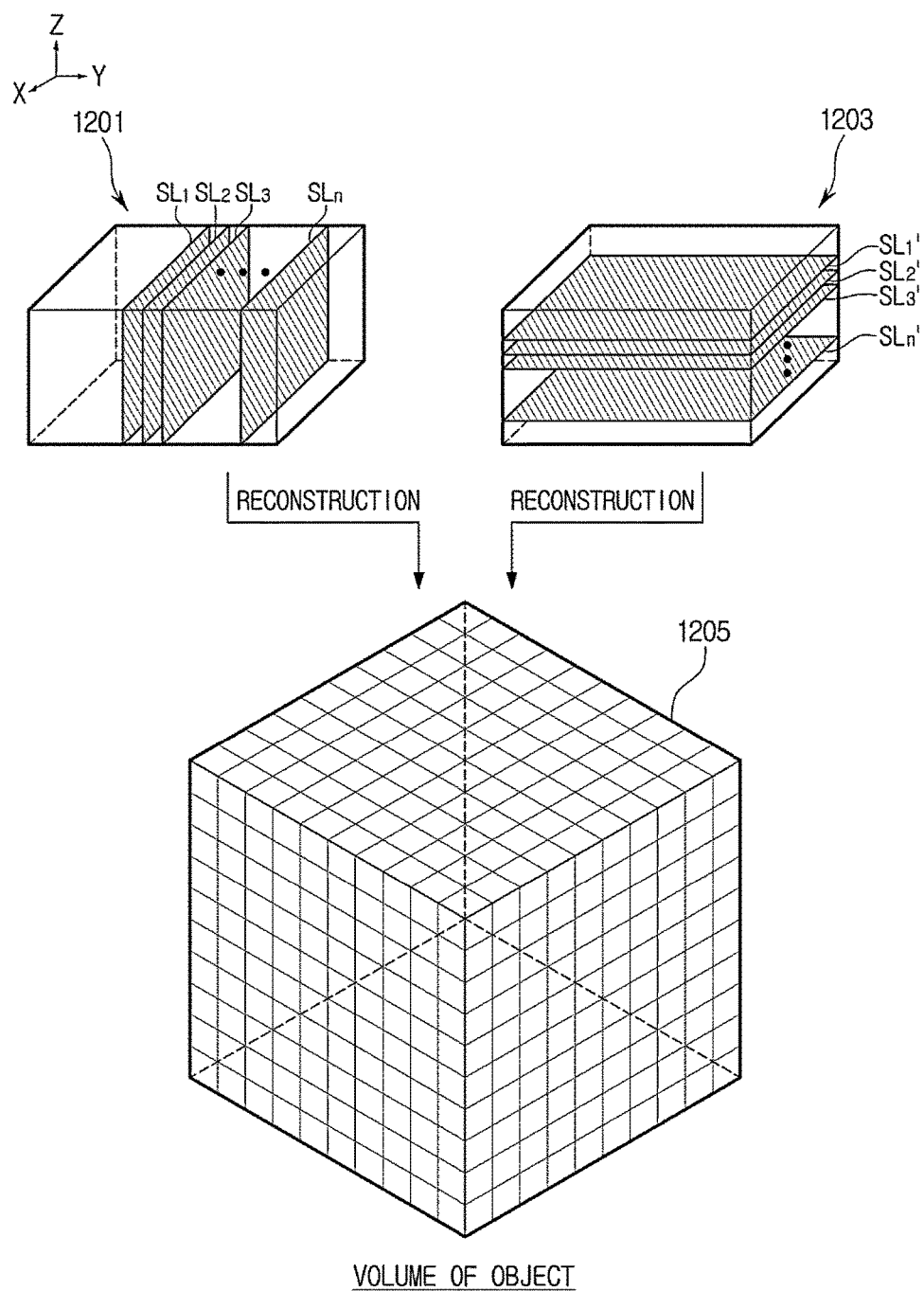
FIG. 12 is a view illustrating a reconstructed volume by using a sectional image of an object according to an exemplary embodiment.

FIG. 11 is a view illustrating a sectional image of an object generated by a 3D reconstructor according to an exemplary embodiment and FIG. 12 is a view illustrating a reconstructed volume by using a sectional image of an object according to an exemplary embodiment.

The 3D reconstructor 121 may generate a sectional image of an object based on projection data of the object and may reconstruct a 3D volume of the object based on the sectional image of the object.

As mentioned above, the scanner 110 may acquire projection data of the object 30 in a plurality of views, which are different from each other, by rotating around the object 30 at a certain angle or by using a structure surrounding the object 30. The data processor 120 may generate a sectional image of the object 30 by reconstructing the projection data transmitted from the scanner 110. In a medical imaging field, the sectional image may be referred to as a slice.

A method of generating sectional images by reconstructing projection data may include an iterative method, matrix inversion, back projection, and Fourier transform, filtered back-projection, and the like.

The iterative method is a method of continuously correcting projection data until data, which are close to the original structure of the object, are acquired. The back projection is a method of returning projection data acquired from a plurality of views to one screen, and the Fourier transform is a method of converting projection data from a spatial domain to a frequency domain. The filtered back projection is a method of back projection after filtering to offset a blur formed around a center of projection data.

For example, when the scanner 110 scans the object 30 while rotating with respect to a Y-axis, or when the scanner 110 has a structure surrounding the object 30 with respect to the Y-axis, the 3D reconstructor 121 may reconstruct projection data acquired by the scanner 110 and may generate sectional images 1101 including n (n being an integer greater than two) sectional images $SL_1, SL_2, SL_3, \ldots SL_n$ in parallel to an X-Z plane and along a Y-axis direction.

The scanner 110 may generate sectional images 1103 including n (n being an integer greater than two) sectional images $SL_1', SL_2', SL_3', \ldots SL_n'$ in parallel to an X-Y plane and along a Z-axis direction.

Particularly, when the scanner 110 scans the object according to CT, MRI, and PET techniques, sectional images 1101 in parallel to an X-Z plane may be acquired, and when the scanner 110 scans the object according to tomosynthesis technique, sectional images 1103 in parallel to an X-Y plane may be acquired.

Scanning techniques and sectional images according to the scanning techniques are not limited thereto. According to various scanning techniques, methods of acquiring sectional images in parallel to a specific plane may be determined as needed.

As illustrated in FIG. 12, the 3D reconstructor 121 may reconstruct a 3D volume of the object by accumulating or stacking a plurality of sectional images. A volume of the object may be represented as volume data, and the volume data may have a structure in which voxels having a scalar value and a vector value are arranged in three dimensions.

As illustrated in FIG. 12, when sectional images 1201 including n sectional images $SL_1, SL_2, SL_3, \ldots SL_n$ in parallel to an X-Z plane are generated, a volume 1205 may be reconstructed by stacking a plurality of sectional images 1201 in a Y-axis direction, and when sectional images 1203 including n sectional images $SL_1', SL_2', SL_3', \ldots SL_n'$ in parallel to an X-Y plane are generated, the volume 1205 may be reconstructed by stacking a plurality of sectional images 1203 in a Z-axis direction.

Figure 13:
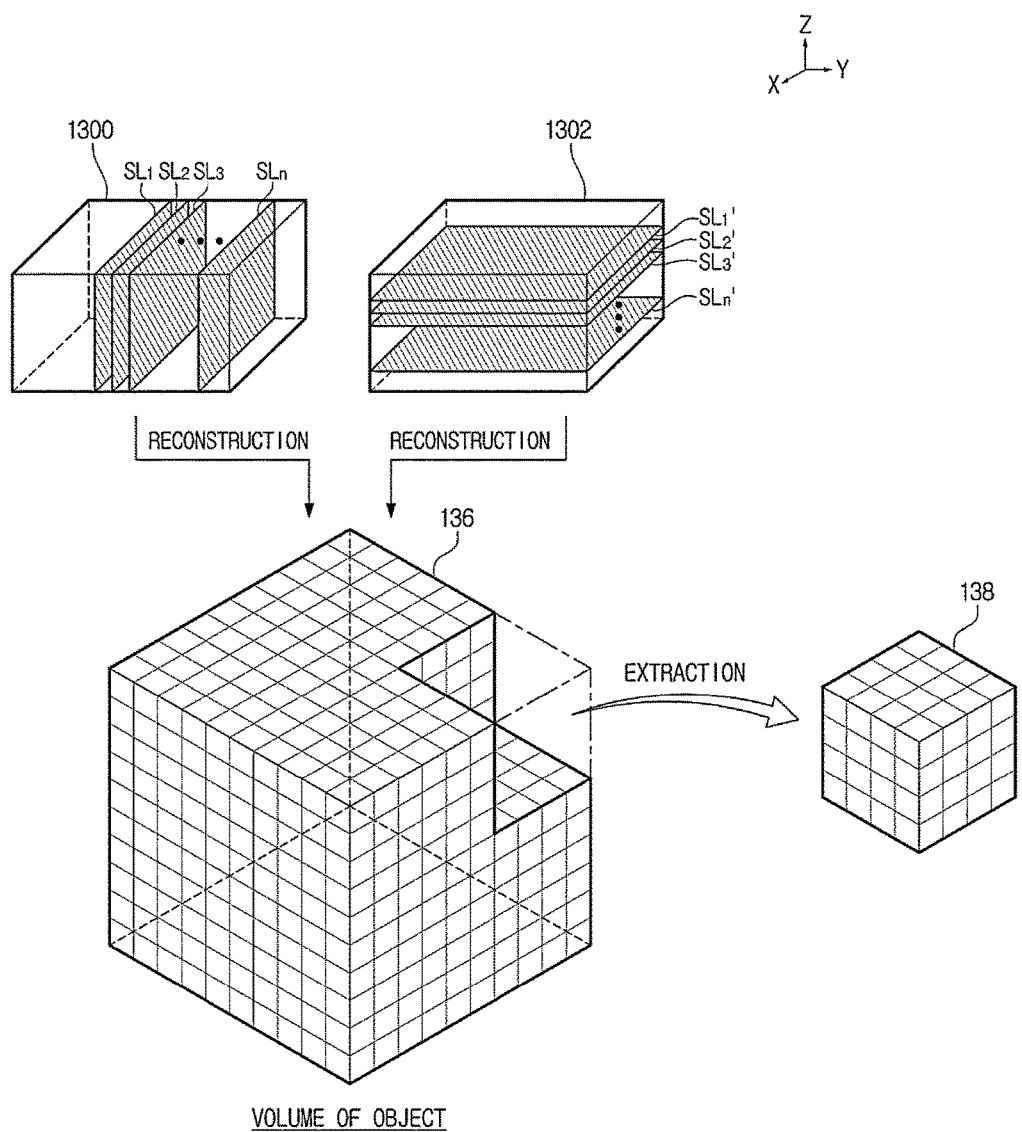
FIG. 13 is a view illustrating a process of extracting a volume of interest from a volume of an object according to an exemplary embodiment.

FIG. 13 is a view illustrating a process of extracting a volume of interest from a volume of an object according to an exemplary embodiment.

As mentioned above, the VOI extractor 122 may extract a volume of interest from a volume of the object. The volume of interest may represent a 3D region of interest and may be determined according to content of diagnosis through medical images. For example, when the object 30 is a breast, the volume of interest may be a region suspected to be microcalcifications. In this case, the volume of interest may be extracted by using a feature of the microcalcifications, which have a high brightness (or intensity) value as compared to a region around the microcalcifications.

In addition, when the object 30 is a lung, the volume of interest may be a region suspected to be a nodule, and when the object 30 is a liver or a stomach, the volume of interest may be a region suspected to be a tumor. That is, a region of the object 30 suspected to include a target substance may be determined as a volume of interest.

As illustrated in FIG. 13, when a volume 136 is reconstructed by stacking a plurality of sectional images 1300 including n sectional images $SL_1, SL_2, SL_3, \ldots SL_n$ and/or a plurality of sectional images 1302 including n sectional images $SL_1', SL_2', SL_3', \ldots SL_n'$, the VOI extractor 112 may extract a volume of interest 138 from the volume 136 by extracting or segmenting voxels suspected to be a target substance and clustering the extracted or segmented voxels or by extracting or segmenting sectional images suspected to include a target substance and clustering the extracted or segmented sectional images.

The reprojector 123 may generate a 2D projection image by projecting the extracted volume of interest 138 in a certain direction. Projection performed in the reprojector 123 may be referred to as "reprojection" to be distinguished from projection performed in the scanner 110. A 2D projection image generated by the reprojection of the reprojector 123 may be referred to as a "2D reprojection image" to be distinguished from a 2D projection image generated by scanning of the scanner 110.

FIGS. 14, 15, 16, and 17 are views illustrating a process of generating a 2D reprojection image by reprojecting a volume of interest according to exemplary embodiments.

The reprojector 123 may generate 2D reprojection images by reprojecting a volume of interest in at least one direction among a plurality of directions. For example, the reprojector 123 may reproject a volume of interest in at least one direction among an X-axis, a Y-axis, and a Z-axis directions, but is not limited thereto. For convenience of illustration, the following exemplary embodiments will be described in which reprojection may be performed in at least one direction among an X-axis, a Y-axis, and a Z-axis directions.

Figure 14:
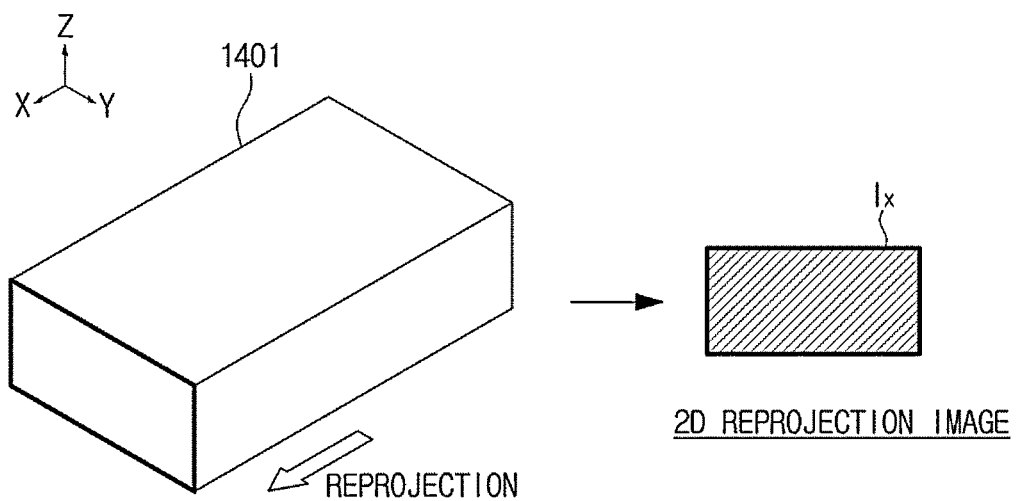
FIGS. 14, 15, 16, and 17 are views illustrating a process of generating a 2D reprojection image by reprojecting a volume of interest according to exemplary embodiments.
Figure 15:
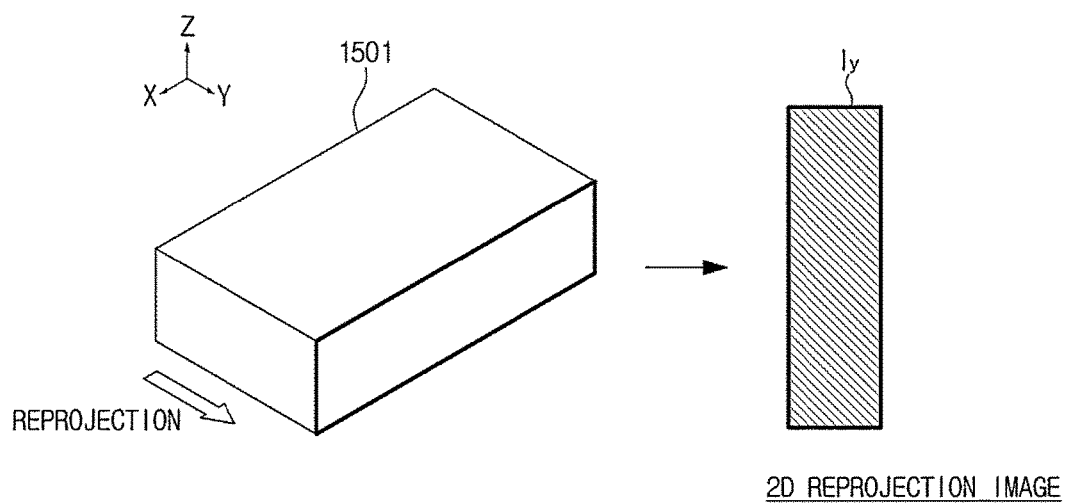
Figure 16:
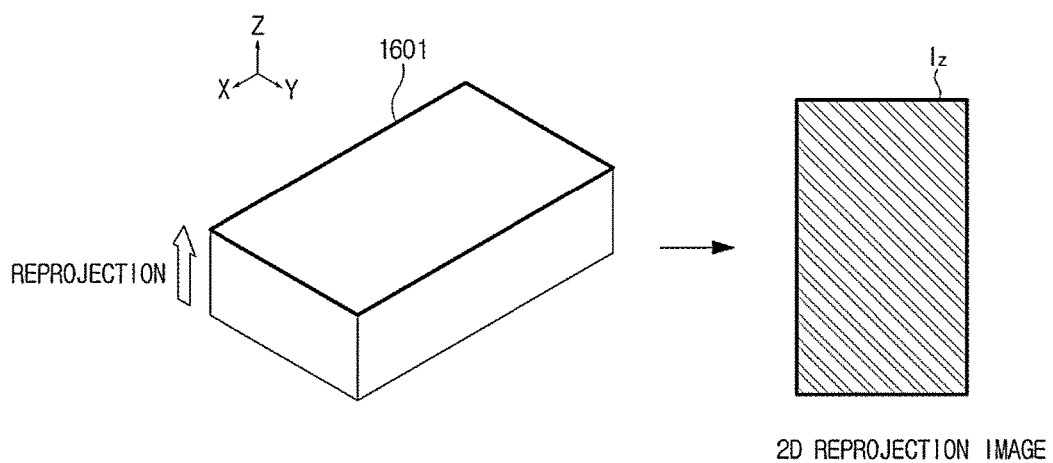

For example, as illustrated in FIG. 14, reprojection images $I_x$ in X-axis may be generated by reprojecting a volume of interest 1401 in an X-axis direction. In another example, as illustrated in FIG. 15, reprojection images $I_y$ in Y-axis may be generated by reprojecting a volume of interest 1501 in a Y-axis direction. In still another example, as illustrated in FIG. 16, reprojection images $I_z$ in Z-axis may be generated by reprojecting a volume of interest 1601 in a Z-axis direction.

Figure 17:
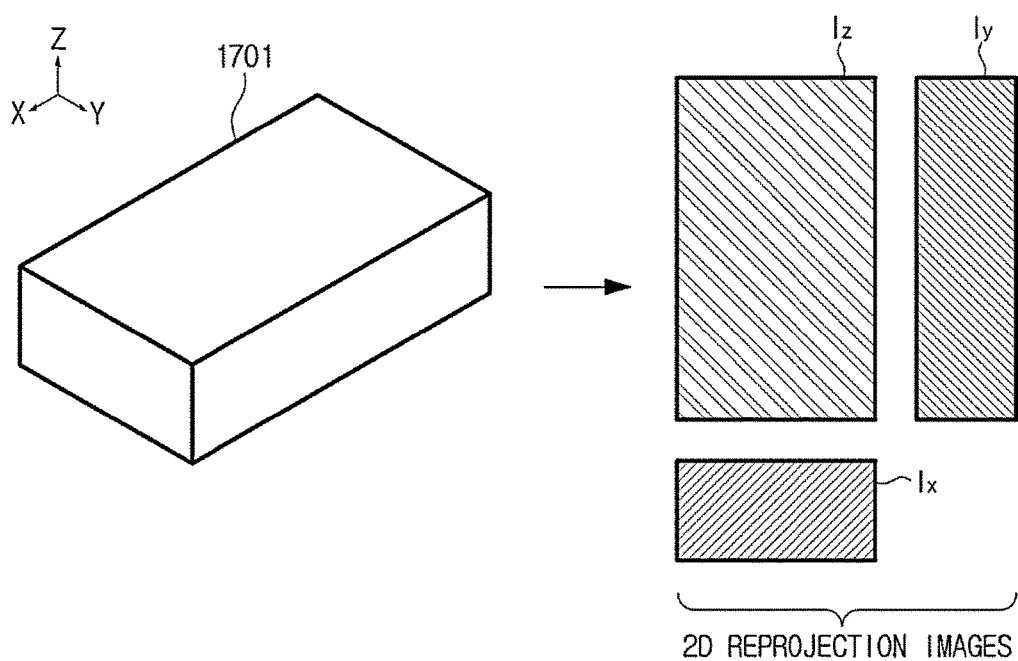

As illustrated in FIG. 17, three 2D reprojection images $I_x$, $I_y$, $I_z$ may be generated by reprojecting a volume of interest 1701 in an X-axis, a Y-axis, and a Z-axis directions, respectively.

Maximum value projection may be employed as one example of reprojection, which is described in detail below.

Figure 18:
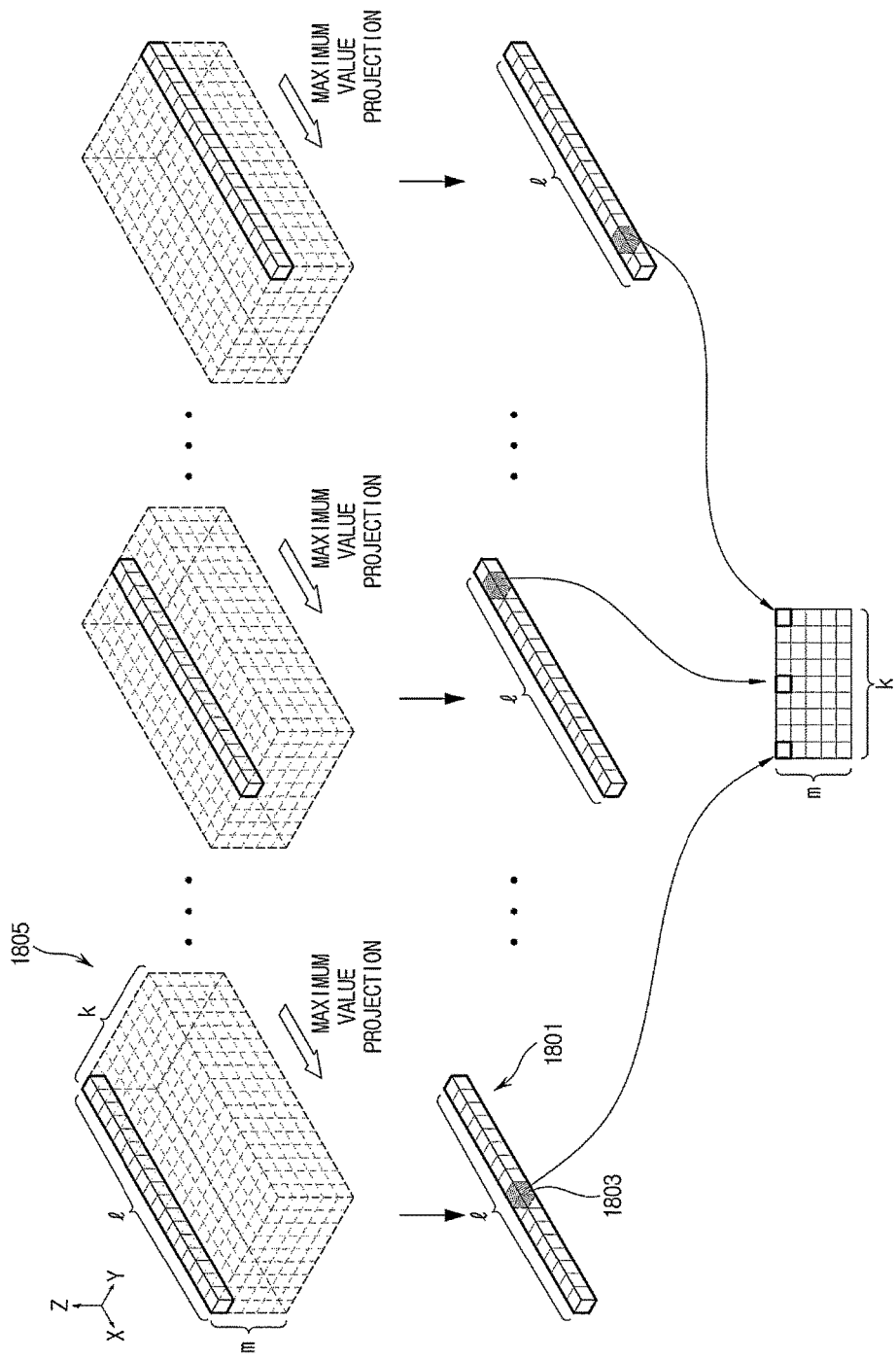
FIG. 18 is a view illustrating a process of performing maximum value projection in an X-axis direction according to an exemplary embodiment.
Figure 19:
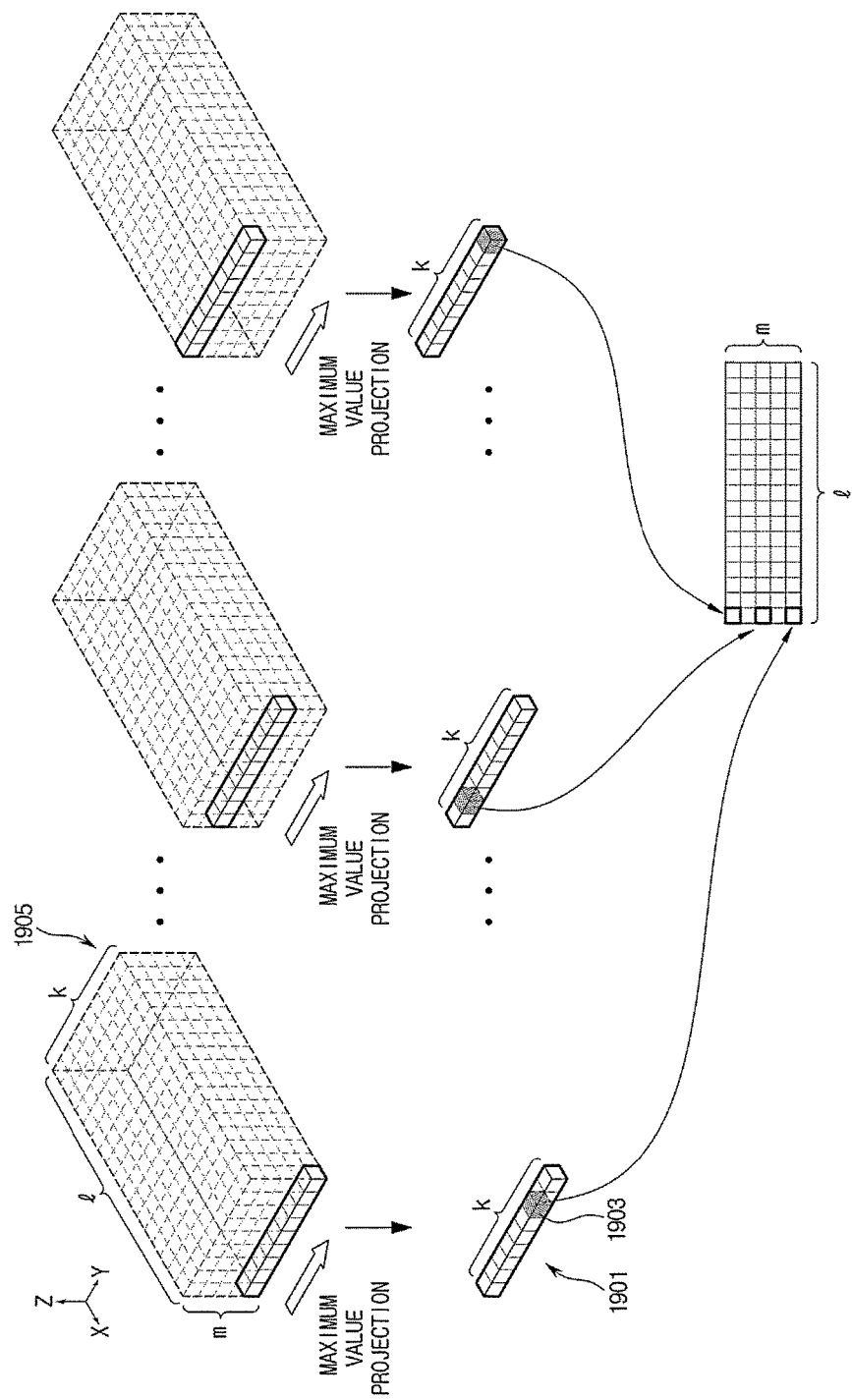
FIG. 19 is a view illustrating a process of performing maximum value projection in a Y-axis direction according to an exemplary embodiment.
Figure 20:
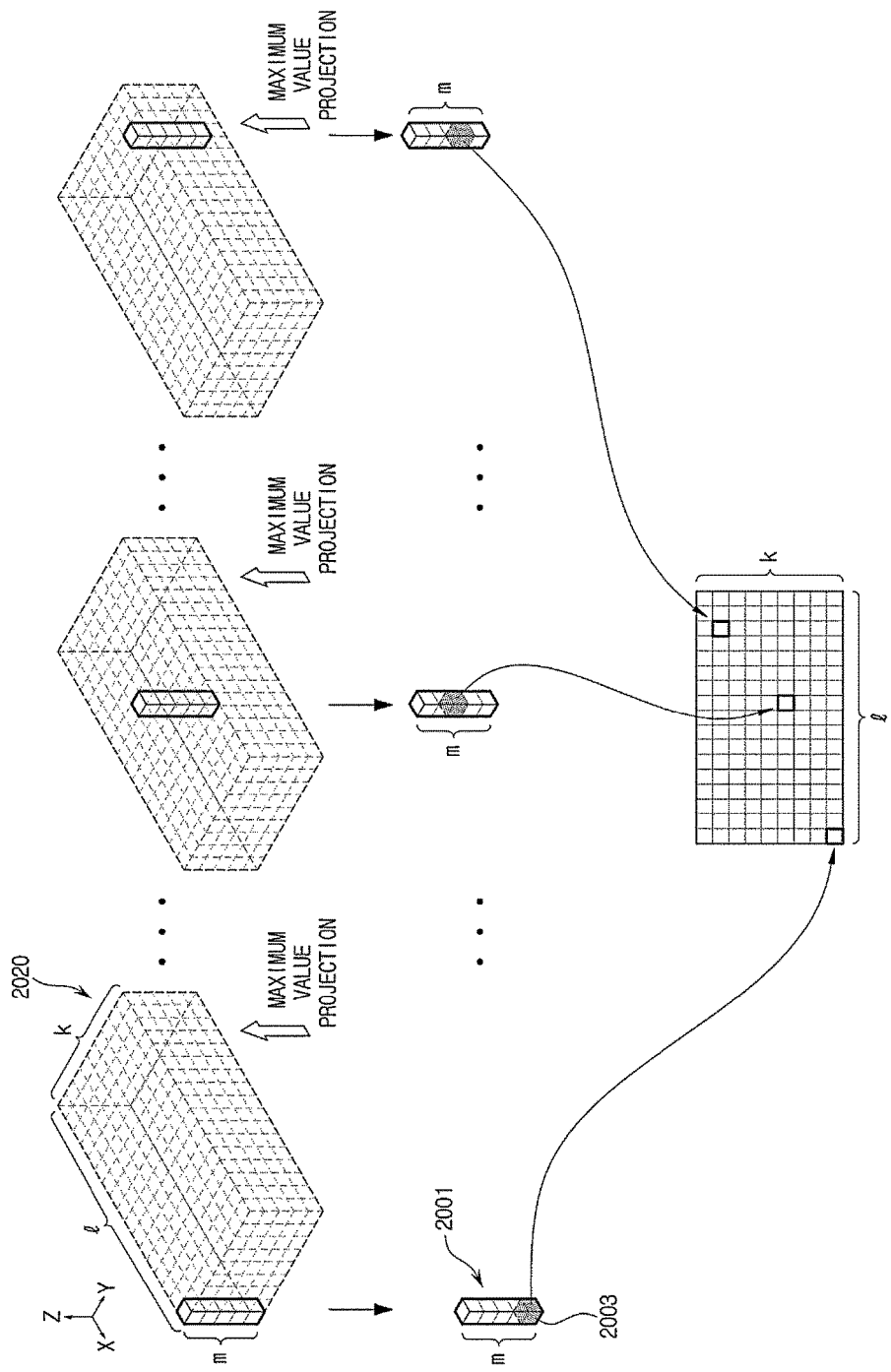
FIG. 20 is a view illustrating a process of performing maximum value projection in a Z-axis direction according to an exemplary embodiment.

FIG. 18 is a view illustrating a process of performing maximum value projection in an X-axis direction according to an exemplary embodiment, FIG. 19 is a view illustrating a process of performing maximum value projection in a Y-axis direction according to an exemplary embodiment, and FIG. 20 is a view illustrating a process of performing maximum value projection in a Z-axis direction according to an exemplary embodiment.

As illustrated in FIG. 18, a case where l×k×m (l, k, m each being an integer equal to or greater than one) voxels arranged in a 3D space form a volume of interest 1805 will be described as one example. A position of each voxel may be displayed in (x, y, z) coordinates.

When performing maximum value projection on a volume of interest 1805 in an X-axis direction, 2D reprojection images containing m×k pixels in parallel to a Y-Z plane (or along the X-axis direction) may be generated. Specifically, the maximum voxel value may be extracted by comparing voxel values of voxels having the same (y, z) coordinates among l×k×m voxels. For example, when a set 1801 of l number of voxels having the same (y, z) coordinates is obtained, a voxel 1803 having the maximum voxel value among the l number of voxels of the set 1801 is extracted. The same process may be performed for each set of voxels having the same (y, z) coordinates.

By using the maximum values extracted from each set of voxels, a 2D reprojection image containing m×k pixels may be generated. A position of each pixel in the 2D reprojection image may be displayed in (y, z) coordinates, and the maximum value extracted from a set corresponding to the same (y, z) coordinates may be determined as a pixel value of corresponding (y, z) coordinates.

As illustrated in FIG. 19, when performing maximum value projection on a volume of interest 1905 in a Y-axis direction, 2D reprojection images containing m×l pixels in parallel to an X-Z plane may be generated. Specifically, the maximum voxel value may be extracted by comparing voxel values of voxels having the same (x, z) coordinates among l×k×m voxels. For example, when a set 1901 of k number of voxels having the same (x, z) coordinates is obtained, a voxel 1903 having the maximum voxel value among the k number of voxels of the set 1901 is extracted. The same process may be performed for each set of voxels having the same (x, z) coordinates.

By using the maximum values extracted from each set of voxels, a 2D reprojection image containing m×l pixels may be generated. A position of each pixels in the 2D reprojection image may be displayed in (x, z) coordinates, and the maximum value extracted from a set corresponding to the (x, z) coordinates may be determined as a pixel value of corresponding (x, z) coordinates.

As illustrated in FIG. 20, when performing maximum value projection on a volume of interest 2020 in a Z-axis direction, 2D reprojection images containing k×l pixels in parallel to an X-Y plane may be generated. Specifically, the maximum voxel value may be extracted by comparing voxel values of voxels having the same (x, y) coordinates among l×k×m voxels. For example, when a set 2001 of k number of voxels having the same (x, y) coordinates is obtained, a voxel 2003 having the maximum voxel value among the m number of voxels of the set 2001 is extracted. The same process may be performed for each set of voxels having the same (x, y) coordinates.

By using the maximum values extracted from each set, a 2D reprojection image containing k×l pixels may be generated. A position of each pixel in the 2D reprojection image may be displayed in (x, y) coordinates, and the maximum value extracted from a set corresponding to the same (x, y) coordinates may be determined as a pixel value of corresponding (x, y) coordinates.

As mentioned above, when maximum value projection of a volume of interest is performed in the reprojector 123, a blur or an artifact of microcalcifications may be reduced, and when feature information is extracted from reprojection images generated by performing maximum value projection, it may be possible to extract discriminating feature information.

The feature analyzer 124 may extract feature information from 2D reprojection images in each direction, and the extracted feature information may be analyzed according to a target substance.

The extraction of the feature information may be performed by using at least one of feature extraction algorithms, such as a spatial gray level dependence (SGLD) matrices method, a run difference method, a Law's texture feature method, an autocorrelation based texture features method, a co-ccurence matrices texture features method, a Moravec's corner detector, a Harris corner detector, a Harris Laplace detector, a Harris Affine detector, a Hessian Affine detector, an edge-based region detector, an intensity-based region detector, a difference of Gaussian operator, a Laplacian of Gaussian operator, a scale invariant feature transform (SIFT) detector and the like.

In addition, the feature extraction algorithm may be selected according to a target substance. For example, when a target substance is microcalcifications in a breast, the spatial gray level dependence (SGLD) matrices method or the Law's texture feature method may be applied.

The above algorithms may be only given as examples of algorithm applicable for the feature analyzer 124, and exemplary embodiments are not limited thereto.

When 2D reprojection images in an X-axis, a Y-axis, and a Z-axis directions are generated in the reprojector 123, the feature analyzer 124 may extract feature information from three 2D reprojection images among the generated 2D reprojection images by applying a feature extraction algorithm.

Since the feature analyzer 124 may extract feature information from 2D reprojection images instead of 3D volume data, an amount of data to be processed may be reduced and a result of the calculation may be quickly acquired.

Figure 21:
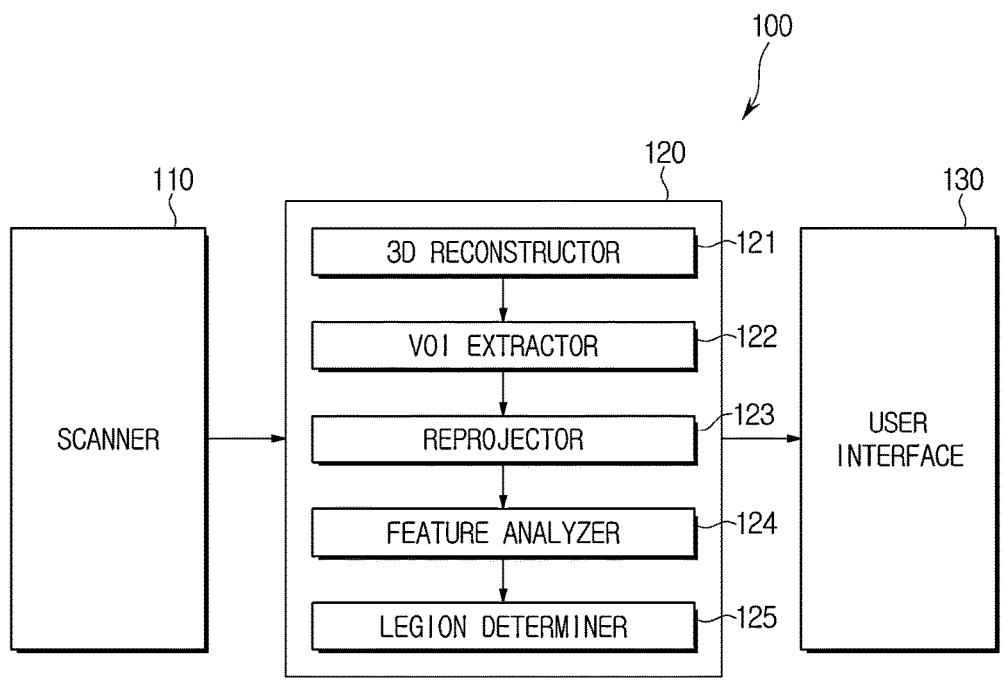
FIG. 21 is a control block diagram illustrating a configuration of a data processor performing computer-aided diagnosis (CAD) according to an exemplary embodiment.

FIG. 21 is a control block diagram illustrating a configuration of a data processor performing computer-aided diagnosis (CAD) according to an exemplary embodiment.

The medical imaging apparatus 100 may perform a computer-aided diagnosis (CAD) to assist diagnosis by a user. For this purpose, the data processor 120 may further include a lesion determiner 125 determining the presence of a lesion by fusing feature information extracted from 2D reprojection images corresponding to each direction. The lesion determiner 125 may perform detection of microcalcifications in a breast, detection of a lung nodule, detection of a colon polyp, and the like.

The lesion determiner 125 may generate a feature vector by fusing feature information extracted from 2D reprojection images corresponding to each direction, and may determine whether a volume of interest is a lesion by using the generated feature vector.

There is no limitation to a method of fusing feature information for the lesion determiner 125. For example, feature information extracted from X-axis reprojection images $I_x$, Y-axis reprojection images $I_y$, and Z-axis reprojection images $I_z$ may be fused to be concatenated.

The lesion determiner 125 may determine a lesion by using a classifier. For example, whether the fused feature information represents a lesion, such as microcalcifications or a nodule, may be determined by using a support vector machine (SVM)

A result of determining a lesion may be provided to a user through a user interface 130 to assist in performing final diagnosis by the user.

The medical imaging apparatus 100 may be provided with image data of the object from the outside, and in this case, the scanner 110 may be omitted in the medical imaging apparatus 100. A series of operations of performing CAD by processing image data provided from the outside may be substantially the same as in the above exemplary embodiments.

Hereinafter, a method of providing a result of the processing of the above-described data processor 120 to a user will be described in detail.

Figure 22:
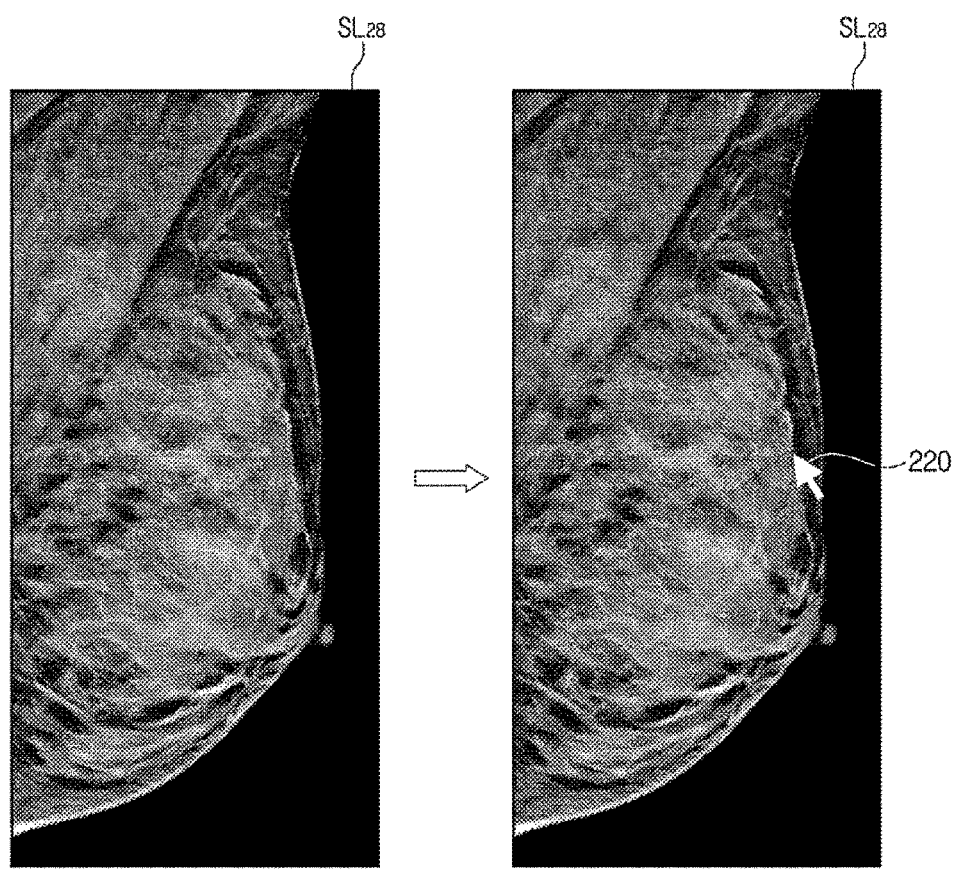
FIGS. 22 and 23 are views illustrating an operation of setting a region of interest by a user according to exemplary embodiments.
Figure 23:
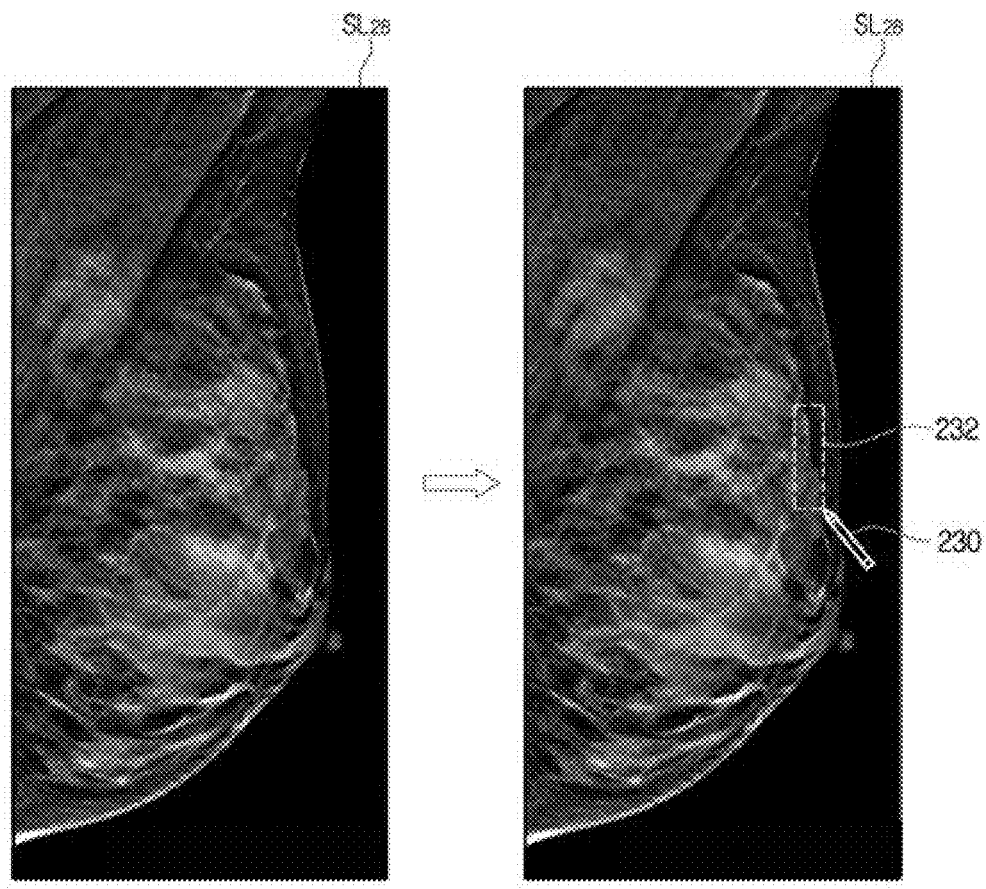
Figure 24:
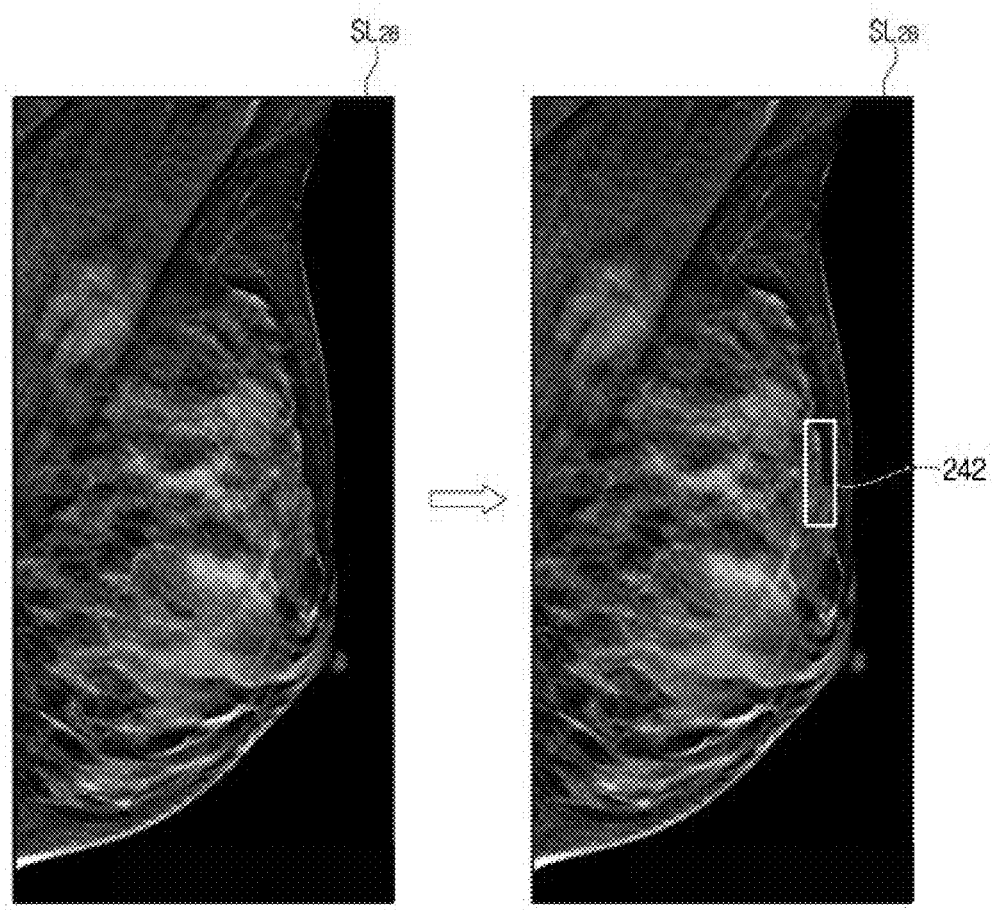
FIG. 24 is a view illustrating an operation of automatic setting a region of interest according to an exemplary embodiment.

FIGS. 22 and 23 are views illustrating operations of setting a region of interest by a user according to exemplary embodiments, and FIG. 24 is a view illustrating an operation of automatic setting a region of interest according to an exemplary embodiment. In the exemplary embodiments of FIGS. 22 to 24, an object may be a breast and a scanner 110 may perform tomosynthesis.

A region of interest may be set by a user and a VOI extractor 122 may extract a volume of interest corresponding to the region of interest set by a user.

For this purpose, a display 131 may display a sectional image $SL_{28}$ of a breast, and the user may confirm the displayed sectional image $SL_{28}$. When a point suspected to be microcalcifications exists in the displayed sectional image $SL_{28}$, the point may be selected by using a pointing device, such as a cursor 220, and a certain region including the selected point may be set as a region of interest. The VOI extractor 122 may extract a volume of interest corresponding to the set region of interest.

Alternatively, as illustrated in FIG. 23, a sectional image $SL_{28}$ of a breast is displayed, and a user may directly draw a certain region 232 including a point suspected to be microcalcifications in the displayed sectional image $SL_{28}$ by using a drawing device 230. The drew certain region 232 may be set as a volume of interest, and the VOI extractor 122 may extract a volume of interest corresponding to the set region of interest.

Alternatively, as illustrated in FIG. 24, a sectional image $SL_{28}$ of a breast is displayed, and the VOI extractor 122 may automatically set a region 242 of interest suspected to be microcalcifications in the sectional image $SL_{28}$ displayed on the display 131, and may mark the region 242 and display to a user.

In FIGS. 22 and 23, the selection of a certain point by using a pointing device such as the cursor 220 and a drawing motion by using the drawing device 230 may be performed through an input unit 132.

Figure 25:
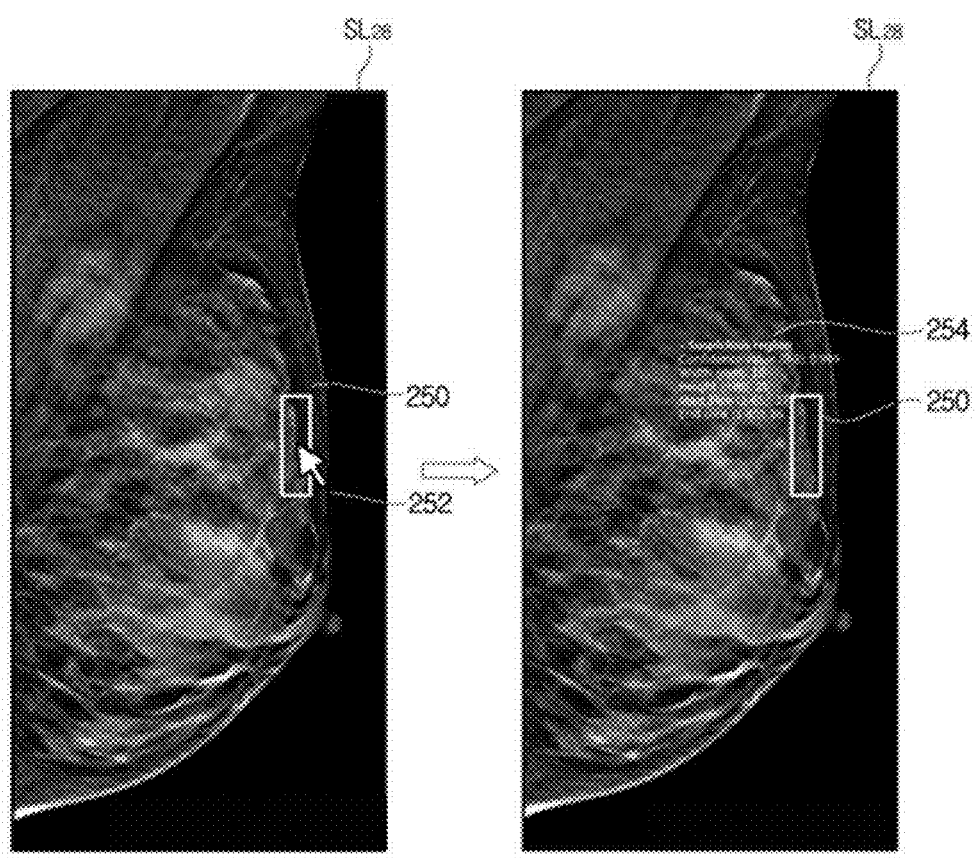
FIGS. 25 and 26 are views illustrating an example of displaying additional information on a display according to exemplary embodiments.
Figure 26:
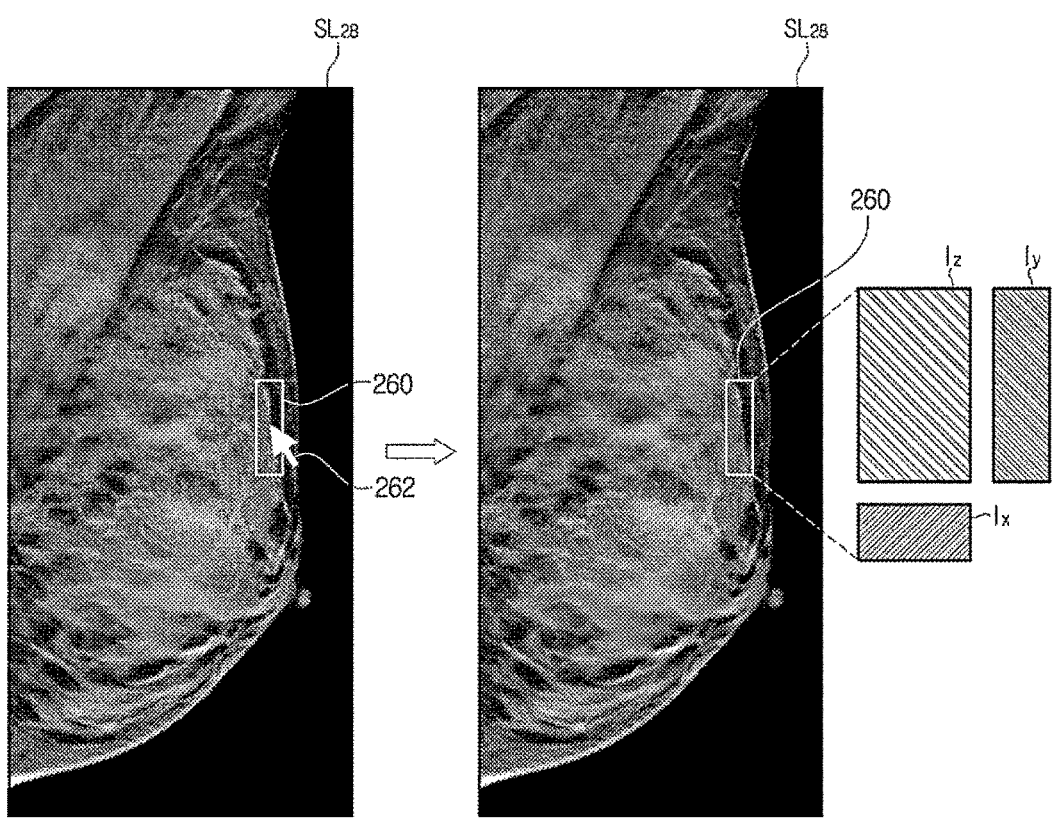

FIGS. 25 and 26 are views illustrating examples of displaying additional information on a display according to exemplary embodiments.

In FIG. 25, when a user selects a region 250 suspected to be microcalcifications in a displayed sectional image $SL_{28}$ by using a cursor 252, the region 250 is set as a region of interest, and the display 131 may display the sectional image $SL_{28}$ with additional information related to the region of interest 250. For example, as illustrated in FIG. 25, information 254 related to a confidence value indicating a probability of the region of interest 250 containing microcalcifications, the width of the region of interest 250, the height of the region of interest 250, a first sectional image (or a start slice) constituting the extracted volume of interest, and a second sectional image (or an end slice) constituting the extracted volume of interest may be displayed on the display 131.

As illustrated in FIG. 26, when a user selects a region 260, which is a region of interest, in a displayed sectional image $SL_{28}$ by using a cursor 262, X-axis reprojection images $I_x$, obtained by projecting an extracted volume of interest corresponding to the region 260 in an X-axis direction, Y-axis reprojection images $I_y$ obtained by projecting the extracted volume of interest in a Y-axis direction, and Z-axis reprojection images $I_z$ obtained by projecting the extracted volume of interest in a Z-axis direction may be displayed on the display 131.

In an exemplary embodiment, information 254 displayed in FIG. 25 and images $I_x$, $I_y$, $I_z$ displayed in FIG. 26 may be displayed together.

Hereinafter, a control method of a medical imaging apparatus according to exemplary embodiments will be described.

To describe the control method of a medical imaging apparatus, the medical imaging apparatus 100 illustrated in FIGS. 1 to 26 may be used. The above description may be applied to exemplary embodiments of the control method of the medical imaging apparatus 100.

Figure 27:
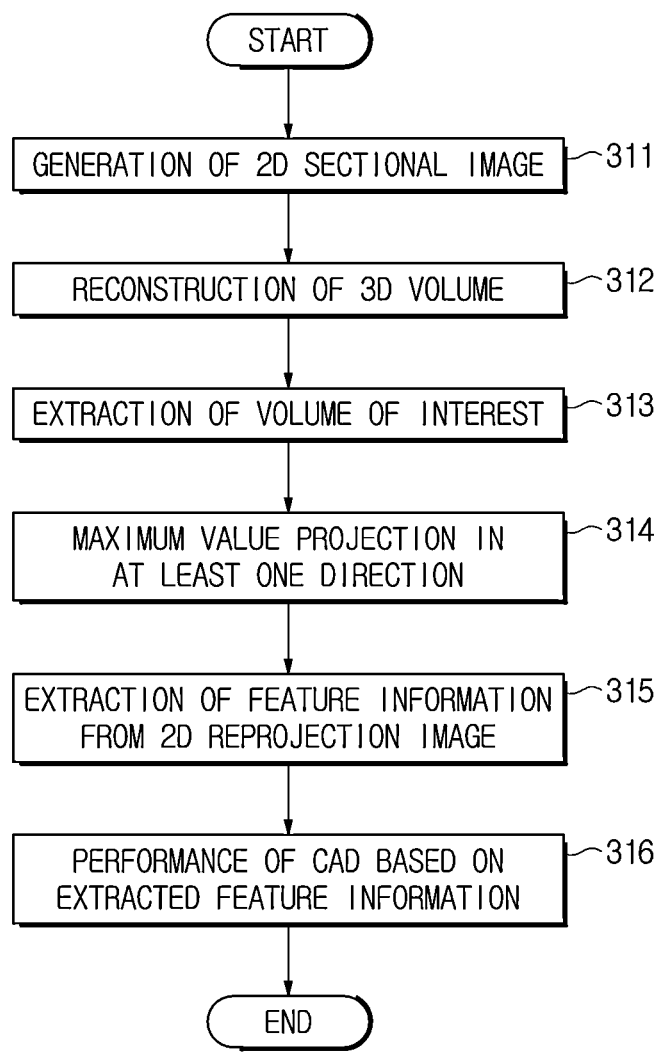
FIG. 27 is a flow chart illustrating a control method of a medical imaging apparatus according to an exemplary embodiment.

FIG. 27 is a flow chart illustrating a control method of a medical imaging apparatus according to an exemplary embodiment.

According to an exemplary embodiment of a control method of the medical imaging apparatus 100, the scanner 110 may acquire image data of an object 30 by scanning the object 30, and may transmit the image data to the data processor 120. Processes illustrated in FIG. 27 may be performed by the data processor 120 receiving image data of the object 30.

Referring to FIG. 27, a 2D sectional image of the object 30 may be generated (operation 311). Particularly, the data processor 120 may generate a 2D sectional image by reconstructing the image data received from the scanner 110, and the image data received from the scanner 110 may be projection data indicating a 2D projection image.

When a sectional image parallel to an X-Z plane is generated, a plurality of sectional images in a Y-axis direction may be generated. When a sectional image parallel to an X-Y plane is generated, a plurality of sectional images in a Z-axis direction may be generated.

A 3D volume of the object 30 may be reconstructed (operation 312). Particularly, the data processor 120 may reconstruct a 3D volume by stacking the plurality of sectional images. When a sectional image parallel to an X-Z plane is generated, a volume may be reconstructed by stacking the plurality of sectional images in a Y-axis direction and when a sectional image parallel to an X-Y plane is generated, a volume may be reconstructed by stacking the plurality of sectional images in a Z-axis direction.

A volume of interest may be extracted from the 3D volume of the object (operation 313). The volume of interest may represent a 3D region of interest, and may be determined according to content of diagnosis through medical images. Particularly, the volume of interest may be extracted by clustering pixels after extracting and segmenting pixels suspected to be a target substance. When a target substance is suspected to be present in the volume of interest, the volume of interest may be extracted by clustering the sectional images after extracting and segmenting sectional images.

A volume of interest may be automatically extracted by the data processor 120 or by a selection from a user. In the case of automatically extracting the volume of interest by the selection from the user, at least one of 2D sectional images of the object 30 may be displayed on the display 131 and when a region of interest is set by a user, a volume of interest corresponding to the set region of interest may be extracted.

Maximum value projection on the volume of interest may be performed in at least one direction (operation 314). For example, maximum value projection may be performed in an X-direction, a Y-direction and a Z-axis directions. Accordingly, three 2D reprojection images corresponding to each direction may be generated.

According to an exemplary embodiment of a control method of a medical imaging apparatus, performing maximum volume projection may be unnecessary, but when performing maximum volume projection, a blur or an artifact of the region of interest may be reduced, and when extracting feature information from reprojection images generated by the maximum value projection, it may be possible to extract discriminating feature information.

Feature information may be extracted from 2D reprojection images (operation 315). When 2D reprojection images are generated in an X-axis, a Y-axis, and a Z-axis directions by the reprojector 123, the feature analyzer 124 may extract feature information from three 2D reprojection images in respective X, Y, Z axis directions by applying a feature extraction algorithm. The extracted feature information may be analyzed according to a target substance.

The extraction of the feature information may be performed by using at least one of feature extraction algorithms, such as a spatial gray level dependence (SGLD) matrices method, a run difference method, a Law's texture feature method, an autocorrelation based texture features method, a co-ccurence matrices texture features method, a Moravec's corner detector, a Harris corner detector, a Harris Laplace detector, a Harris Affine detector, a Hessian Affine detector, an edge-based region detector, an intensity-based region detector, a difference of Gaussian operator, a Laplacian of Gaussian operator, a scale invariant feature transform (SIFT) detector and the like.

In addition, the feature extraction algorithm may be selected according to a target substance. For example, when a target substance is microcalcifications in a breast, the spatial gray level dependence (SGLD) matrices method or the Law's texture feature method may be applied.

The above algorithms may be only given as examples of algorithm applicable for the feature analyzer 124, and exemplary embodiments are not limited thereto.

A computer-aided diagnosis (CAD) may be performed by using the extracted feature information (operation 316). According to an exemplary embodiment of a control method of a medical imaging apparatus, a computer-aided diagnosis (CAD) may be performed to assist diagnosis by a user. Particularly, a feature vector may be generated by fusing feature information extracted from 2D reprojection images corresponding to each direction, and it may be determined whether the volume of interest is a lesion by applying a classifier, such as SVM, to the generated feature vector.

Figure 28:
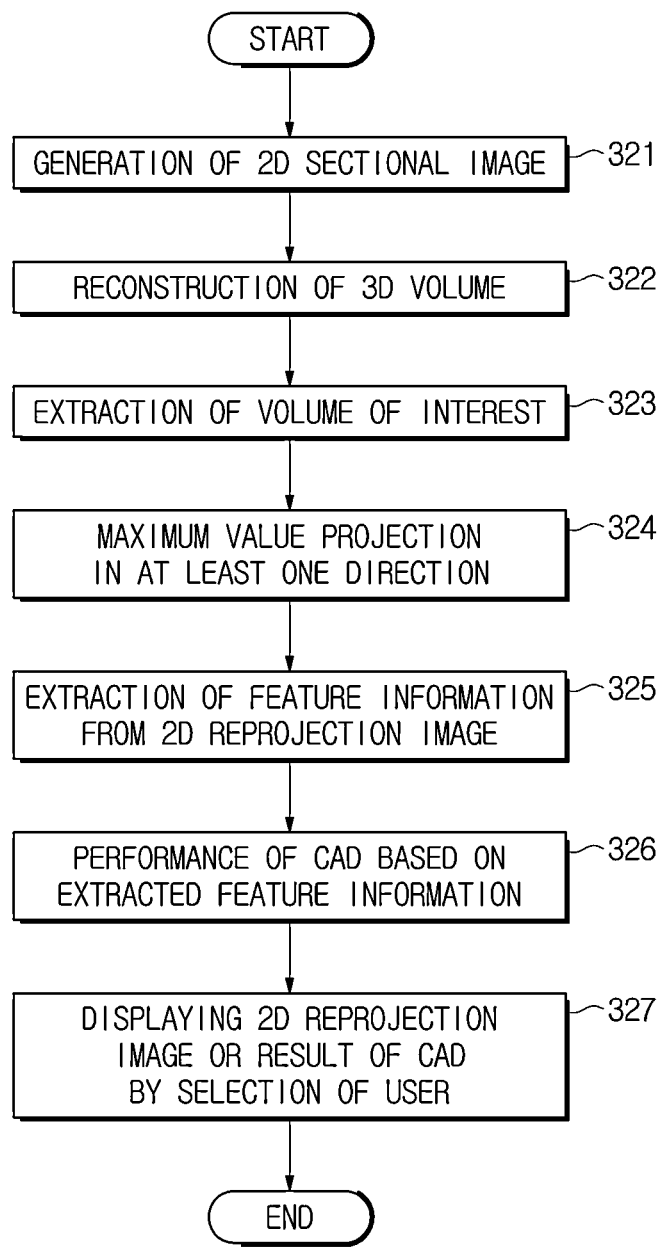
FIG. 28 is a flow chart illustrating a method of providing additional information to a user cording to a control method of a medical imaging apparatus according to an exemplary embodiment.

FIG. 28 is a flow chart illustrating a method of providing additional information to a user according to a control method of a medical imaging apparatus according to an exemplary embodiment.

In FIG. 28, operations including generating a 2D sectional image (operation 321) to performing CAD by using extracted feature information (operation 326) may be substantially the same as those described in operations 311 to 316 of FIG. 27. Thus, repetitive descriptions thereof may be omitted.

A 2D reprojection image and a result of CAD may be displayed according to a selection by a user (operation 327). Referring again to FIGS. 25 and 26, in a case where an object is a breast and the scanner performs tomosynthesis to acquire projection data, the display 131 may display additional information of the region of interest when a user selects a region suspected to be microcalcifications as the region of interest.

For example, as illustrated in FIG. 25, information related to a confidence value indicating a probability of a region of interest containing microcalcifications, the width of the region of interest, the height of the region of interest, a first sectional image (or start slice) constituting the extracted volume of interest and a second sectional image (or an end slice) constituting the extracted volume of interest may be displayed on the display 131.

In addition, as illustrated in FIG. 26, X-axis reprojection images $I_x$ obtained by projecting an extracted volume of interest in an X-axis direction, Y-axis reprojection images $I_y$ obtained by projecting the extracted volume of interest in a Y-axis direction, and Z-axis reprojection images $I_z$ obtained by projecting the extracted volume of interest in a Z-axis direction may be displayed on the display 131.

In an exemplary embodiment, information 254 displayed in FIG. 25 and images $I_x$, $I_y$, $I_z$ displayed in FIG. 26 may be displayed together.

According to an exemplary embodiment of a control method of a medical imaging apparatus, an amount of data to be processed may be reduced and the calculation result may be quickly acquired by extracting feature information from 2D reprojection images instead of 3D volume data.

In addition, according to an exemplary embodiment, a 2D reprojection image may be generated by performing maximum volume projection on a volume of interest so that a blur or an artifact of the region of interest may be reduced.

When extracting feature information from reprojection images generated by maximum value projection, it may be possible to extract discriminating feature information.

The described-above exemplary embodiments and advantages are merely exemplary and are not to be construed as limiting. The present teaching can be readily applied to other types of apparatuses. The description of exemplary embodiments is intended to be illustrative, and not to limit the scope of the claims, and many alternatives, modifications, and variations will be apparent to those skilled in the art.

What is claimed is:

1. A medical imaging apparatus comprising:
   a scanner configured to acquire projection data of an object in a plurality of directions;
   a display configured to display a sectional image generated based on the projection data;
   a processor configured to, in response to receiving an input of selecting a region of interest in the displayed sectional image, generate a volume of interest corresponding to the region of interest, generate two-dimensional (2D) reprojection images by reprojecting the volume of interest through maximum value projection in two or more directions, and control the display to display at least one of the 2D reprojection images,
   wherein the processor is further configured to extract feature information from the 2D reprojection images in which a maximum value in each of the two or more directions is extracted from voxels of the volume of interest, and
   wherein the processor is further configured to generate a feature vector by fusing the feature information extracted from the 2D reprojection images reprojected in the two or more directions, and determine whether a certain substance exists in the volume of interest based on the generated feature vector.

2. The medical imaging apparatus of claim 1, wherein the processor is configured to generate an X-axis reprojection image by reprojecting the volume of interest in an X-axis direction, a Y-axis reprojection image by reprojecting the volume of interest in a Y-axis direction, and a Z-axis reprojection image by reprojecting the volume of interest in a Z-axis direction.

3. The medical imaging apparatus of claim 1, wherein the processor is configured to generate a three-dimensional (3D) volume based on the projection data and extract the volume of interest from the 3D volume.

4. The medical imaging apparatus of claim 1, wherein the processor is configured to determine whether the certain substance exists in the volume of interest by applying a classifier to the generated feature vector.

5. The medical imaging apparatus of claim 1, wherein the processor is configured to perform computer aided diagnosis (CAD) based on the extracted feature information.

6. The medical imaging apparatus of claim 1, further comprising:
   an input unit configured to receive the input of selecting the region of interest from a user.

7. The medical imaging apparatus of claim 1, wherein the display is further configured to display the at least one of the 2D reprojection images together with the sectional image.

8. The medical imaging apparatus of claim 7, wherein the display is further configured to display at least one of information related to a size of the region of interest, information related to the sectional image corresponding to the volume of interest, and information related to a probability of the certain substance being present in the volume of interest.

9. A medical imaging apparatus comprising:
   a display configured to display a sectional image generated based on projection data;
   a processor configured to, in response to receiving an input of selecting a region of interest in the displayed sectional image, generate a volume of interest corresponding to the region of interest, generate 2D reprojection images by reprojecting the volume of interest through maximum value projection in two or more directions, and control the display to display at least one of the 2D reprojection images,
   wherein the processor is further configured to extract feature information from the 2D reprojection images in which a maximum value in each of the two or more directions is extracted from voxels of the volume of interest, and
   wherein the processor is further configured to generate a feature vector by fusing the feature information extracted from the 2D reprojection images reprojected in the two or more directions, and determine whether a certain substance exists in the volume of interest based on the generated feature vector.

10. The medical imaging apparatus of claim 9, wherein the display is further configured to display the at least one of the 2D reprojection images together with the sectional image.

11. The medical imaging apparatus of claim 10, wherein, the display is configured to display at least one of information related to a size of the region of interest, information related to the sectional image corresponding to the volume of interest, and information related to a probability of the certain substance being present in the volume of interest in response to the displayed region of interest being selected by a user.

12. The medical imaging apparatus of claim 9, wherein the processor is configured to generate an X-axis reprojection image by reprojecting the volume of interest in an X-axis direction, a Y-axis reprojection image by reprojecting the volume of interest in a Y-axis direction, and a Z-axis reprojection image by reprojecting the volume of interest in a Z-axis direction.

13. The medical imaging apparatus of claim 12, wherein the display is configured to display the X-axis reprojection image, the Y-axis reprojection image, and the Z-axis reprojection image.

14. A control method of a medical imaging apparatus comprising:
   displaying a sectional image generated based on projection data;
   in response to receiving an input of selecting a region of interest in the displayed sectional image, generating a volume of interest based on the projection data of an object;
   generating 2D reprojection images by reprojecting the volume of interest through maximum value projection in two or more directions and displaying at least one of the 2D reprojection images;
   extracting feature information from the 2D reprojection images in which a maximum value in each of the two or more directions is extracted from voxels of the volume of interest; and
   generating a feature vector by fusing the feature information extracted from the 2D reprojection images reprojected in the two or more directions and determining whether a certain substance exists in the volume of interest based on the generated feature vector.

15. The control method of claim 14, wherein the generating the 2D reprojection images comprises generating an X-axis reprojection image by reprojecting the volume of interest in an X-axis direction, generating a Y-axis reprojection image by reprojecting the volume of interest in a Y-axis direction, and generating a Z-axis reprojection image by reprojecting the volume of interest in a Z-axis direction.

16. The control method of claim 14, wherein the determining whether the certain substance exists in the volume of interest comprises:
   determining whether the certain substance exists in the volume of interest by applying a classifier to the generated feature vector.

17. The control method of claim 14, wherein the generating the volume of interest comprises:
   generating a 3D volume based on the projection data; and
   extracting the volume of interest from the 3D volume.

18. The control method of claim 17, wherein the displaying the at least one of 2D reprojection images comprises displaying the at least one of the 2D reprojection images together with the sectional image.

19. The control method of claim 18, further comprising:
   displaying at least one of information related to a size of the region of interest, information related to the sectional image corresponding to the volume of interest, and information related to a probability of the certain substance being present in the volume of interest.

* * * * *